US012599757B2

(12) United States Patent
King et al.

(10) Patent No.: US 12,599,757 B2
(45) Date of Patent: Apr. 14, 2026

(54) FABRICATION METHOD FOR COMPLEX, RE-ENTRANT 3D MICROSCALE STRUCTURES

(71) Applicant: THE CHARLES STARK DRAPER LABORATORY, INC., Cambridge, MA (US)

(72) Inventors: Daniel Frederick King, Watertown, MA (US); David J. Carter, Concord, MA (US); Corin Williams, Framingham, MA (US); Stephanie Lynne Golmon, Arlington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 155 days.

(21) Appl. No.: 18/431,205

(22) Filed: Feb. 2, 2024

(65) Prior Publication Data

US 2024/0181234 A1     Jun. 6, 2024

Related U.S. Application Data

(63) Continuation-in-part of application No. 17/855,081, filed on Jun. 30, 2022.

(Continued)

(51) Int. Cl.
*A61M 37/00*          (2006.01)

(52) U.S. Cl.
CPC . *A61M 37/0015* (2013.01); *A61M 2037/0053* (2013.01); *A61M 2207/10* (2013.01)

(58) Field of Classification Search
CPC ................. A61M 37/0015; A61M 2037/0053
See application file for complete search history.

(56) References Cited

U.S. PATENT DOCUMENTS 1,455,129 A * 5/1923 Venable ............. G11B 23/0057
                                                        428/64.2
3,729,041 A * 4/1973 Kubota .................... B05D 7/57
                                                        152/DIG. 12

(Continued)

FOREIGN PATENT DOCUMENTS

WO       2014144937 A1     9/2014

OTHER PUBLICATIONS

International Search Report and Written Opinion re App. No. PCT/US2022/035772 mailed Oct. 19, 2022.

(Continued)

*Primary Examiner* — Nicholas Krasnow
(74) *Attorney, Agent, or Firm* — Brooks Kushman P.C.

(57)          ABSTRACT

A bilayer mold for forming polymer microstructures is provided. The bilayer mold includes a rigid plastic cylinder having slots defined along an outer periphery of the rigid plastic cylinder; and a layer of plastic elastic polymer material disposed within the slots and having indents defined therethrough and in the rigid plastic cylinder. The indents have a first profile extending through the layer of plastic elastic polymer and terminating within the rigid plastic cylinder. A metal polymer structure profile is also provided using laser-etching of a desired shape for the features of the microstructures in a metallic foil, followed by further refining of the features. The polymer and metal microstructures can be formed on the surface of a stent to facilitate retention of the stent.

6 Claims, 13 Drawing Sheets

Related U.S. Application Data

(60) Provisional application No. 63/483,110, filed on Feb. 3, 2023, provisional application No. 63/218,024, filed on Jul. 2, 2021.

(56) References Cited

U.S. PATENT DOCUMENTS

| | | | | |
|---|---|---|---|---|
| 7,832,251 | B2 * | 11/2010 | Gong | B29C 59/021 |
| | | | | 29/515 |
| 9,060,842 | B2 | 6/2015 | Karp et al. | |
| 9,511,554 | B2 * | 12/2016 | Dave | A61F 2/915 |
| 10,537,721 | B2 * | 1/2020 | Ueno | A61M 37/0015 |
| 10,675,452 | B2 * | 6/2020 | Syrek | A61M 37/00 |
| 10,791,779 | B2 | 10/2020 | Carter et al. | |
| 12,514,958 | B2 * | 1/2026 | Zhang | A61L 27/54 |
| 2004/0052885 | A1 * | 3/2004 | Lee | B29C 43/222 |
| | | | | 425/369 |
| 2006/0091584 | A1 * | 5/2006 | Lyapko | B29C 43/18 |
| | | | | 264/237 |
| 2006/0122687 | A1 * | 6/2006 | Bassler | C22C 45/10 |
| | | | | 219/121.72 |
| 2006/0204738 | A1 | 9/2006 | Dubrow et al. | |
| 2007/0293938 | A1 * | 12/2007 | Gale | A61F 2/90 |
| | | | | 623/1.15 |
| 2009/0125118 | A1 * | 5/2009 | Gong | A61F 2/0077 |
| | | | | 623/23.7 |
| 2009/0133817 | A1 * | 5/2009 | Sabaria | B29C 39/24 |
| | | | | 264/225 |
| 2009/0256287 | A1 * | 10/2009 | Fu | C08G 77/24 |
| | | | | 528/33 |
| 2014/0148897 | A1 | 5/2014 | Matheny | |
| 2014/0217449 | A1 * | 8/2014 | Yamaguchi | H10H 20/82 |
| | | | | 428/156 |
| 2014/0249623 | A1 | 9/2014 | Matheny | |
| 2017/0027682 | A1 * | 2/2017 | Merk | A61F 2/07 |
| 2017/0105724 | A1 | 4/2017 | Limem et al. | |
| 2020/0086101 | A1 | 3/2020 | Yang et al. | |
| 2020/0163785 | A1 | 5/2020 | Schorer et al. | |
| 2023/0277828 | A1 * | 9/2023 | Liu | B29C 33/42 |
| | | | | 604/173 |
| 2025/0090350 | A1 * | 3/2025 | Dong | A61F 2/0077 |

OTHER PUBLICATIONS

Mahdavi, A. et a. "A biodegradable and biocompatible gecko-inspired tissue adhesive." PNAS, 2008, vol. 105. No. 7; 2307-2312. Published Feb. 19, 2008.
Chu et al. "Separable Arrowhead Microneedles." J Control Release. Feb. 10, 2011; 149(3): 242-249.
Yang, S. et al. "A bio-inspired swellable microneedle adhesive for mechanical interlocking with tissue." Nat Commun 4, 1702 (2013). Published Apr. 16, 2013.

* cited by examiner

100 μm — · — · —          WD = 5.5 m          Mag = 189 X          Signal A = InLens
                          Ext I Monitor = 195.3 μA          EHT = 5.00 kV          Vacuum Mode = High Vacuum 20 μm          WD = 8.0 m          Mag = 240 X          Signal A = SE2
               Ext I Monitor = 199.0 μA          EHT = 5.00 kV          Vacuum Mode = High Vacuum 20 μm          WD = 10.4 m          Mag = 311 X          Signal A = SE2
Ext I Monitor = 195.3 μA     EHT = 5.00 kV   Vacuum Mode = High Vacuum 20 μm          WD = 10.5 m          Mag = 278 X          Signal A = SE2
Ext I Monitor = 195.2 μA     EHT = 5.00 kV   Vacuum Mode = High Vacuum

Figure 7: Fabricated polymer and metal MANTIS microstructures.
(A) Metal microstructure X. (B) Metal microstructure Y. (C) ~1 mm
tall linear structure created with a razor blade. (D) ~150 μm tall
pillars with re-entrant profiles created with a tungsten needle.

1. Cylinder of machinist's wax

2. Mill slots corresponding to stent connection points

3. Apply plastic-elastic membrane to slots

4. Indent into bilayer on slots to form completed mold

5. Place mold inside of stent and mold polymer into slot regions

FABRICATION METHOD FOR COMPLEX, RE-ENTRANT 3D MICROSCALE STRUCTURES

CROSS-REFERENCE TO RELATED APPLICATIONS

This application is a continuation-in-part of U.S. patent application Ser. No. 17/855,081, titled "MICROSTRUCTURES FOR LONG-TERM MECHANICAL ADHESION TO TISSUE" filed Jun. 30, 2022, which claims priority under 35 U.S.C. § 119(e) to U.S. Provisional Patent Application Ser. No. 63/218,024, titled "MICROSTRUCTURES FOR LONG-TERM MECHANICAL ADHESION TO TISSUE," filed Jul. 2, 2021, both of which are incorporated by reference herein in their entirety for all purposes. This application also claims priority under 35 U.S.C. § 119(e) to U.S. Provisional Patent Application Ser. No. 63/483,110, titled "FABRICATION METHOD FOR COMPLEX, RE-ENTRANT 3D MICROSCALE STRUCTURES" filed Feb. 3, 2023, which is also incorporated by reference herein in its entirety for all purposes.

STATEMENT REGARDING FEDERALLY SPONSORED RESEARCH

This invention was made with government support under Grant No. W81XWH2010295 awarded by the U.S. Department of Defense (DoD). The government has certain rights in the invention.

TECHNICAL FIELD

Aspects and embodiments disclosed herein relate to biocompatible adhesives. In particular, aspects and embodiments disclosed herein relate to biocompatible adhesive substrates for long-term mechanical adhesion to tissue.

SUMMARY

In accordance with one aspect, there is provided a biocompatible adhesive. The biocompatible adhesive may comprise a substrate and a plurality of micro-scale elements extending from a surface of the substrate having a length selected to puncture a layer of a target tissue. At least some of the micro-scale elements may comprise at least one protrusion dimensioned to anchor the biocompatible adhesive to the target tissue.

The biocompatible adhesive may further comprise a therapeutically active agent coated on a surface of at least some of the plurality of micro-scale elements.

The biocompatible adhesive may further comprise a deployable element configured to deliver a therapeutically active agent to the target tissue.

The therapeutically active agent may be an anti-inflammatory, antimicrobial, or antiseptic agent.

In some embodiments, the biocompatible adhesive may be permanently attachable to the target tissue.

In some embodiments, the biocompatible adhesive may be reversibly attachable to the target tissue.

In some embodiments, the biocompatible adhesive may be biodegradable.

In some embodiments, the biocompatible adhesive may be non-biodegradable.

In some embodiments, the plurality of micro-scale elements may be formed of a polymeric material.

In some embodiments, the plurality of micro-scale elements may be formed of a metal material.

In some embodiments, the plurality of micro-scale elements may be rotationally symmetric.

In some embodiments, the plurality of micro-scale elements may have a rectangular or triangular cross-sectional area.

In some embodiments, the at least one protrusion may be arrowhead-shaped.

In some embodiments, the at least one protrusion may be hook-shaped.

In some embodiments, the at least one protrusion may be ring-shaped.

In some embodiments, the at least one protrusion may be positioned at a distal end of the micro-scale element.

In some embodiments, the at least one protrusion may be positioned along a base of the micro-scale element.

In some embodiments, the plurality of micro-scale elements may have a base width to element length ratio of 1:2-1:10.

In some embodiments, the plurality of micro-scale elements may have a base angle of about 90°, the base angle being defined between a plane of the substrate in an extended conformation and a direction of the extension of the micro-scale elements from the substrate.

In some embodiments, the plurality of micro-scale elements may have a base angle of less than 90°, the base angle being defined between a plane of the substrate in an extended conformation and a direction of the extension of the micro-scale elements from the substrate.

In some embodiments, the plurality of micro-scale elements may have an element length to protrusion length ratio of 1.1:1 to 6:1.

In some embodiments, the at least one protrusion may be a lateral protrusion.

In some embodiments, the at least one protrusion may be a radial protrusion.

In some embodiments, the biocompatible adhesive is coupled to a surface of a medical device assembly and positioned to attach the medical device assembly to the target tissue.

In accordance with another aspect, there is provided a medical device assembly. The medical device assembly may comprise a first component. The medical device assembly may comprise a first biocompatible adhesive comprising a substrate and a plurality of micro-scale elements extending from a surface of the substrate having a length selected to puncture a layer of a target tissue. At least some of the micro-scale elements may comprise at least one protrusion dimensioned to anchor the first biocompatible adhesive to the target tissue. The first biocompatible adhesive may be coupled to a surface of the first component and positioned to attach the medical device assembly to the target tissue.

In some embodiments, the medical device assembly may comprise a second component.

The medical device assembly may comprise a second biocompatible adhesive coupling the first component to the second component.

In some embodiments, the medical device assembly may be implantable.

In some embodiments, the medical device assembly may be a prosthetic heart valve.

In some embodiments, the first component may be a suture skirt and the second component may be a stent.

In some embodiments, the target tissue is live tissue.

In some embodiments, the target tissue is bioprosthetic tissue.

In some embodiments, the bioprosthetic tissue is a vein.

In some embodiments, the bioprosthetic tissue is a valve.

In accordance with another aspect, there is provided a method of facilitating attachment of a medical device assembly comprising a first component to a target tissue of a subject. The method may comprise providing a first biocompatible adhesive comprising a substrate and a plurality of micro-scale elements extending from a surface of the substrate having a length selected to puncture a layer of the target tissue, at least some of the micro-scale elements comprising at least one protrusion dimensioned to anchor the first biocompatible adhesive to the target tissue. The method may comprise providing instructions to couple the first biocompatible adhesive to a surface of the first component of the medical device assembly. The first biocompatible adhesive may be positioned to attach the medical device assembly to the target tissue.

In some embodiments, the medical device assembly may further comprise a second component. The method may further comprise providing a second biocompatible adhesive. The method may comprise providing instructions to couple the second component to the first component with the second biocompatible adhesive.

In accordance with another aspect, there is provided a method of facilitating treatment of a wound on a target tissue of a subject. The method may comprise providing a biocompatible adhesive comprising a substrate and a plurality of micro-scale elements extending from a surface of the substrate having a length selected to puncture a layer of the target tissue, at least some of the micro-scale elements comprising at least one protrusion dimensioned to anchor the biocompatible adhesive to the target tissue. The method may comprise providing instructions to anchor the biocompatible adhesive to the target tissue thereby treating the wound.

In some embodiments, the biocompatible adhesive may further comprise a therapeutically active agent coated on a surface of at least some of the plurality of micro-scale elements.

In some embodiments, the biocompatible adhesive may further comprise a deployable element configured to deliver a therapeutically active agent to the target tissue.

In some embodiments, the therapeutically active agent may be an anti-inflammatory, antimicrobial, or antiseptic agent.

In some embodiments, treating the wound may comprise facilitating at least partial closure of the wound.

In some embodiments, the target tissue may be an external tissue.

In some embodiments, the target tissue may be an internal tissue.

In some embodiments, the biocompatible adhesive may be reversibly attachable to the target tissue.

In some embodiments, the biocompatible adhesive may be permanently attachable to the target tissue.

In some embodiments, the biocompatible adhesive may be biodegradable.

In some embodiments, the biocompatible adhesive may be non-biodegradable.

In some embodiments, the plurality of micro-scale elements may have a length selected to puncture at least two layers of the target tissue.

The method may further comprise anchoring the biocompatible adhesive to the target tissue.

In some embodiments, anchoring the biocompatible adhesive to the target tissue provides substantially simultaneous attachment of the biocompatible adhesive to the target tissue.

In accordance with one aspect, there is provided a biocompatible adhesive. The biocompatible adhesive may comprise a substrate and a plurality of micro-scale elements extending from a surface of the substrate having a length selected to puncture a layer of a target material. At least some of the micro-scale elements may comprise at least one protrusion dimensioned to anchor the biocompatible adhesive to the target material.

In accordance with another aspect, there is provided a medical device assembly. The medical device assembly may comprise a first component. The medical device assembly may comprise a first biocompatible adhesive comprising a substrate and a plurality of micro-scale elements extending from a surface of the substrate having a length selected to puncture a layer of a target material. At least some of the micro-scale elements may comprise at least one protrusion dimensioned to anchor the first biocompatible adhesive to the target material. The first biocompatible adhesive may be coupled to a surface of the first component and positioned to attach the medical device assembly to the target material.

In some embodiments, the target material may be a synthetic material.

In accordance with another aspect, there is provided a method of fabricating biocompatible metal microstructures. The method comprises generating geometries of interest with CAD software; laser cutting into metallic foils of a desired thickness; and refining the features using methods such as chemical etching and/or electropolishing.

In accordance with another aspect, there is provided a method of fabricating biocompatible polymer microstructures. The method comprises creating re-entrant prototype molds using a rigid plastic material such as low durometer machinist's wax and a plastic elastic material such as 0.004" polyethylene sheets; laminating the plastic elastic material to the top of the wax using heat and pressure; and allowing the wax to flow and create a secure, flat surface. Additionally, a razor or tungsten needle is used to indent into the bilayer, creating a re-entrant mold microstructure profile. Biocompatible polymer materials, including but not limited to urethanes or silicones, are then poured into the mold and cured. To remove the structures, the wax is dissolved in acetone and the polyethylene is peeled away. The bilayer mold may be used with a stent, and the bilayer mold may be formed on the stent to form the polymer microstructure on the stent in one-step, or may be used to prefabricate the polymer microstructures for mechanical attachment to the stent.

The disclosure contemplates all combinations of any one or more of the foregoing aspects and/or embodiments, as well as combinations with any one or more of the embodiments set forth in the detailed description and any examples.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3 B is a cross-sectional view of the schematic drawing of the portion of the medical device assembly of FIG. 3 A;

FIG. 3 C is a schematic drawing of a portion of a medical device assembly, according to one embodiment;

FIG. 3 D includes a schematic drawing of a portion of a medical device assembly and a cross-sectional view of the portion of the medical device assembly, according to one embodiment;

DETAILED DESCRIPTION

Figure 1:
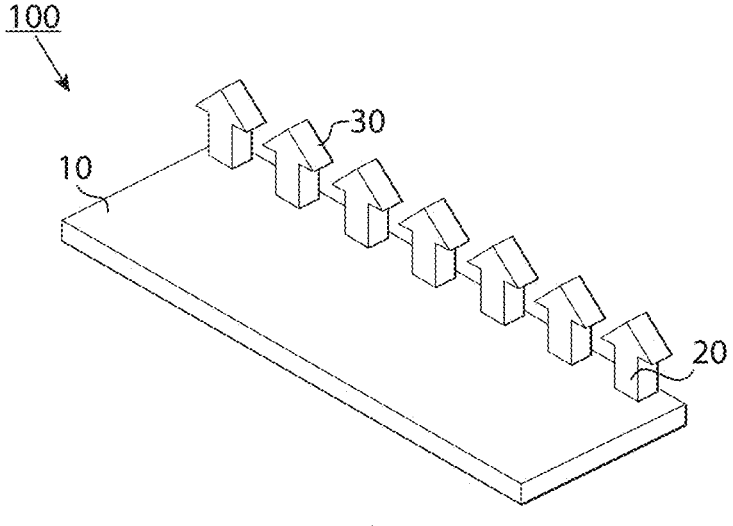
FIG. 1 is a schematic drawing of a biocompatible adhesive, according to one embodiment.

Open wounds are injuries involving an external or internal break in body tissue. Treatment of open wounds often involves washing and disinfecting the wound to remove any foreign matter and closing the wound with a substrate. Common wound closure substrates include, for example, adhesive, staples, and sutures.

Medical devices are implants or prosthetics placed inside or on the surface of the body to replace a missing biological structure, support a damaged biological structure, or enhance an existing biological structure. Medical devices may be used to perform a variety of functions, such as diagnostic, therapeutic, and/or monitoring functions. Medical devices can be placed permanently or removed after a period of time. Placement of medical devices is often performed by attaching the device to a target tissue with adhesive or sutures. Certain devices are also manufactured by coupling one or more parts to each other with adhesive or sutures.

For closure of severe wounds and placement of critical or delicate medical devices, current methods generally involve suturing by hand. However, hand suturing requires significant skill, leading to extended times in surgery. Hand suturing is not practical in the field or at the point of injury.

Additionally, during device manufacturing, suturing produces low yield because the process is time consuming and has low tolerance for error leading to high manufacturing costs. Devices that require integration of two unlike materials, such as metal and soft tissue or soft material, are especially challenging.

Referring to one exemplary situation, the assembly of bioprosthetic heart valves currently requires suturing by hand, a labor-intensive process performed by highly trained technicians. Suturing along every strut and node can require more than 1,000 sutures per device and over 20 hours of skilled labor. During the procedure, the tissue must not be fully punctured to avoid valve leakage and failure upon implantation. Due to the delicate nature of this process, there is typically low yield, for example, 50% or less.

Practitioners have searched for alternatives to hand suturing that may be applied with a lower skill level and in less time, resulting in cost savings to the patient. However, the few alternatives to hand suturing on the market have not been shown to be adequate replacements for all applications. For instance, conventional adhesives (such as cyanoacrylate ("Super glue"), Bioglue™ (CryoLife, Inc., Kennesaw, Ga.), and Coseal™ (Baxter International Inc., Deerfield, Ill.)) typically fall into two categories. Some conventional adhesives provide a strong bond but are too stiff for delicate tissues. Other conventional adhesives are dynamic and flexible but provide only a weak bond. Neither category of conventional adhesives will provide suitable adhesion for a moving tissue, such as a heart, lung, or muscular tissue.

Other proposed solutions, such as mussel-based and slug slime bio-inspired adhesives, do not provide adequate adhesion to compliant wet surfaces and typically require chemical reactions or materials that are not translatable in the clinic.

Conventional methods do not generally provide adequate adhesion or integration of two unlike materials. Integrating soft and hard materials or metal to a tissue or polymer is often a requirement when implanting medical devices in the body. When the environment is mechanically demanding (such as bone or heart tissue), device failure can be catastrophic. For example, migration of a medical device from the implantation site is a significant concern for transcatheter heart valves and self-expanding stents placed in other lumens of the body (such as blood vessels, gastrointestinal system tissues, and the esophagus). Adhesives that do not adequately integrate unlike materials are generally inadequate for such applications.

Most, if not all, conventional medical adhesives are biodegradable. Biodegradable adhesives are more generally used for fast healing or superficial wound closure. For devices that are intended to be implanted long-term, such as heart valves, biodegradable adhesives are generally inadequate.

Thus, there is a need for an improved method of adhesion that can provide suitable adhesion to wet surfaces, integration of unlike materials, adequate strength and flexibility, and long-term or permanent adhesion.

Additionally, infections resulting from both wound treatment and placement of medical devices are common. Wound infections generally occur when bacteria and other pathogenic microorganisms grow within the damaged tissue of the wound. Device associated infections generally occur as a result of pathogenic microorganism colonization at the placement site. Medical devices may also be rejected by surrounding tissues when placement of the device triggers a disproportionate immune response. There is a need for an improved method of adhesion that reduces the risk of an adverse reaction to wound treatment and medical device placement.

In accordance with one aspect, there is provided a biocompatible adhesive. The biocompatible adhesives disclosed herein contain engineered microstructures that support mechanical adhesion to a target tissue or target material, such as a component of a medical device. Thus, the biocompatible adhesives disclosed herein do not generally rely on chemical or other adhesion mechanisms to provide attachment. Although in certain embodiments, the biocompatible adhesives disclosed herein may be supplemented with chemical or other adhesion mechanisms. For instance, in certain embodiments, the biocompatible adhesives may be supplemented with sutures (significantly reducing the overall number of sutures) and/or a chemical or conventional adhesive coating.

The biocompatible adhesives disclosed herein may be applied with low skill level and provide rapid adhesion, reducing labor times. In certain embodiments, the biocompatible adhesives disclosed herein may provide substantially simultaneous attachment upon application. The biocompatible adhesives disclosed herein may provide strong adhesion to compliant wet surfaces such as internal organs and wounds, adhesion and integration of two unlike materials, flexible but strong dynamic adhesion to preserve tissue flexibility and movement, and optional long-lasting or permanent adhesion.

The biocompatible adhesives disclosed herein may comprise a substrate and a plurality of micro-scale elements extending from a surface of the substrate. The substrate may be a substantially planar structure. The biocompatible adhesive may be a single-sided adhesive. In such embodiments, the plurality of micro-scale elements may extend from one surface of the substrate. The biocompatible adhesive may be a double-sided adhesive. In such embodiments, the plurality of micro-scale elements may extend from two opposite surfaces of the substrate.

In certain embodiments, the biocompatible adhesive may have a backing layer positioned on an adhesive side of the adhesive. For instance, a backing layer may be positioned adjacent a distal end of the micro-scale elements. The backing layer may provide protection for the micro-scale elements, for example, during storage or transport. The backing layer may be easily removable prior to application of the biocompatible adhesive. The backing layer may have a smooth surface. The backing layer may have an indented surface configured to mate with the micro-scale elements.

The micro-scale elements may be engineered for mechanical attachment to a selected target tissue. Mechanical attachment to tissue material generally requires puncture and/or penetration of at least one layer of the tissue. As disclosed herein, "puncture" or "puncturing" may refer to any insertion into a layer, including partial insertion. As disclosed herein, "penetrate" or "penetration" may refer to passage through a layer.

The layer of the tissue may be an external or superficial layer of the tissue. The layer may be, for example, an external layer of the tissue, such as an external fibrous layer. The layer may be, for example, a superficial layer of the tissue, such as a superficial fibrous layer, cell layer (e.g., epithelial cell layer or connective cell layer), or adventitial layer (e.g., adventitial layer of a blood vessel, including puncturing an adventitial layer of the blood vessel and puncturing a medial layer of the blood vessel). In some embodiments, mechanical attachment may include penetrating a superficial mucosal layer to puncture and/or penetrate a fibrous layer of the target tissue.

Referring specifically to skin tissue as one exemplary target tissue, an epidermal layer covers an exterior surface of the skin. An adhesive effective for external wound closure may include micro-scale elements engineered to puncture and/or penetrate the epidermal layer of the skin. Other bodily tissues have similar external layers. The biocompatible adhesives disclosed herein are generally engineered to puncture and/or penetrate at least one layer of a selected target tissue.

The target tissue may be any bodily structure capable of providing mechanical resistance. The target tissue may comprise any bodily tissue. The biocompatible adhesives disclosed herein may be engineered to provide adhesion to delicate tissues, such as gastrointestinal and pulmonary tissues, dynamic tissues, such as cardiac and muscular tissues, and dense tissues, such as skeletal and connective tissues. Exemplary target tissues include cardiac tissue, pulmonary tissue, skeletal tissue, muscular tissue, connective tissue, nervous tissue, gastrointestinal tissue, ocular tissue, dental tissue, and others.

The target tissue may be a native tissue. For example, the target tissue may be a live tissue of the subject. In other embodiments, the target tissue may be non-native tissue, for example, a bioprosthetic tissue. Bioprosthetic tissues may be previously implanted foreign tissues. The bioprosthetic tissues may be implanted at the time of implanting the biocompatible adhesive. The bioprosthetic tissues may comprise donor tissue or bioengineered tissue. The donor tissue may be, for example, allogeneic or xenogeneic tissue. The bioengineered tissue may be at least partially synthetic tissue. The bioengineered tissue may comprise autologous, allogeneic, or xenogeneic tissue.

In some embodiments, the micro-scale elements may have a length selected to puncture or penetrate a layer of the target tissue, for example, an external or superficial layer of the target tissue. The length may be selected to avoid puncturing or penetrating a specific layer of the target tissue. For example, the length may be selected to avoid puncturing a nerve, e.g., a layer of the target tissue containing nerves. The length may be selected to avoid puncturing a fluid-containing lumen, such as a blood vessel or intestine. The length may be selected to avoid puncturing or penetrating any non-target layer of the target tissue. In certain embodiments, the micro-scale elements may have a length selected to puncture or penetrate more than one layer of the target tissue, for example, at least two layers of the target tissue.

The disclosure refers generally to attachment to a target tissue. However, it should be understood that micro-scale elements may be engineered for mechanical attachment to any target material. Thus, any embodiments disclosed herein which refer to a target tissue may be used for attachment to any target material. The target material may be any non-tissue material. The target material may be a synthetic material. The target material may be, for example, a polymeric material, a metal material, or any other material. Such biocompatible adhesives may be used to attach any non-tissue target structure. In exemplary embodiments, such biocompatible adhesives may be used to attach a component of a medical device assembly.

Figures 4, 5:
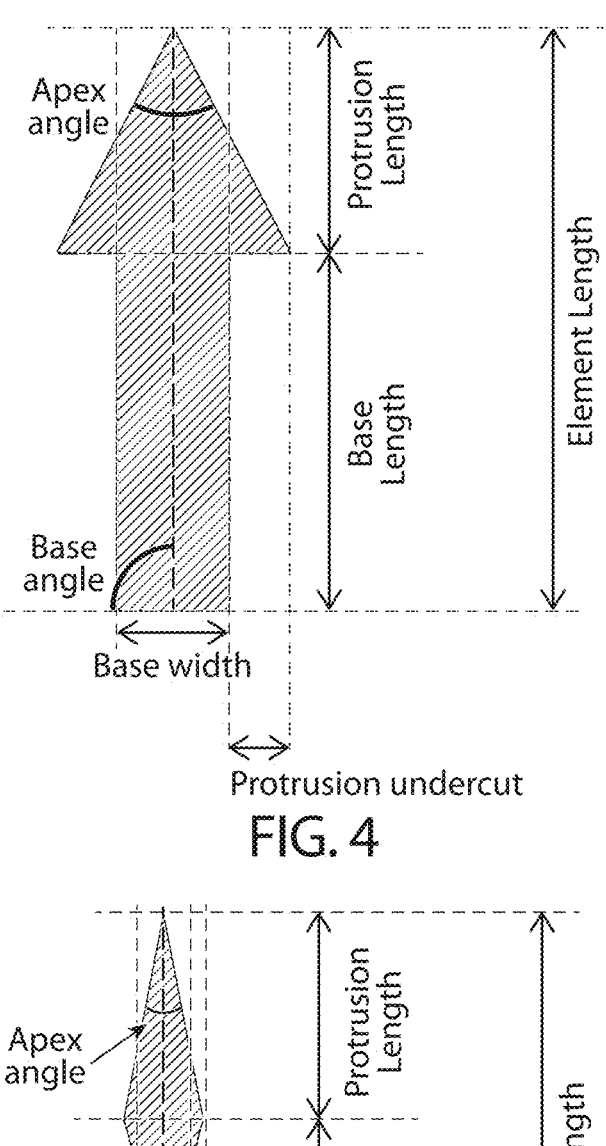
FIG. 4 is a schematic drawing of a micro-scale element, according to one embodiment.
FIG. 5 is a schematic drawing of a micro-scale element, according to one embodiment.
Figure 6:
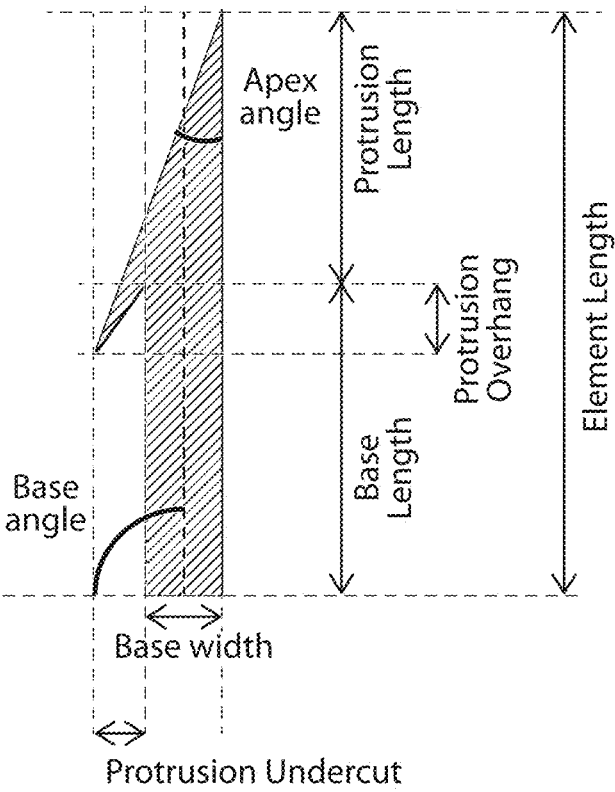
FIG. 6 is a schematic drawing of a micro-scale element, according to one embodiment.

The micro-scale elements may be defined by length and width dimensions of a base portion and an optional protrusion portion, as shown in FIGS. 4-6. While the micro-scale elements may be dimensioned to correspond with the selected target tissue, for example, may have any shape or size selected to provide adhesion to the target tissue, exemplary dimensions are described herein. It should be understood that the dimensions described herein are exemplary and the biocompatible adhesive may be engineered for mechanical attachment to any target tissue.

The length of the micro-scale elements may be defined from the proximal end of the micro-scale elements adjacent to the substrate to the distal end of the micro-scale elements. The length of the micro-scale elements may be from about one micrometer to several hundred micrometers. Exemplary micro-scale elements may have a length from less than 1 µm, 1 µm-1,000 µm, 10 µm-750 µm, 10 µm-500 µm, 10 µm-300 µm, 10 µm-250 µm, or 10 µm-150 µm, for example, 10 µm-50 µm, 50 m-100 µm, 100 µm-150 µm, 120 m-150 µm, 150 µm-250 µm, 250 µm-500 µm, 500 µm-750 µm, or 750 µm-1,000 µm. In certain embodiments, the length of the micro-scale element is defined by the length of a base of the micro-scale element plus the length of a protrusion, as shown in FIGS. 4-6.

The micro-scale elements may have a base width selected to provide adequate adhesion with the target tissue. The base width may be selected to provide adequate adhesion while not incurring damage to the target tissue. The base width of the micro-scale elements may be defined by a representative dimension of the proximal end of the micro-scale elements adjacent to the substrate. For example, a conical micro-scale element may have a base width defined by the diameter of the proximal end of the micro-scale element. Similarly, a rectangular pyramid micro-scale element may have a base width defined by the diagonal of the rectangular cross-section proximal end of the micro-scale element and a triangular pyramid micro-scale element may have a base defined by the height of the triangular cross-section of the proximal end of the micro-scale element. Thus, in certain embodiments, the micro-scale element may be rotationally symmetric, having a circular cross-sectional area. In other embodiments, the micro-scale element may have a rectangular or triangular cross-sectional area. The micro-scale elements may have a cross-sectional area of any shape. The micro-scale elements may have a base width of less than 1 µm, 1 µm-100 µm, 10 µm-100 µm, 20 µm-100 µm, or 40 µm-80 µm, for example, 1 µm-60 µm, 10 µm-60 µm, m-60 µm, or 20 µm-40 µm.

The micro-scale elements may have a profile engineered to puncture or penetrate and anchor the target tissue. In some embodiments, the plurality of micro-scale elements may be formed of a short extrusion. Exemplary short extrusions may have a base width to element length ratio of 1:2-1:5, for example 1:2-1:4. In some embodiments, the plurality of micro-scale elements may be formed of a long extrusion. Exemplary long extrusions may have a base width to element length ratio of 1:6-1:10, for example, 1:6-1:8 or 1:8-1:10. Thus, the micro-scale elements may have a base width to element length ratio of 1:2-1:10.

Thus, the base may be defined by a representative dimension of the distal end of the micro-scale elements. The representative dimension may be, for example, a diameter, diagonal, or height, as previously described. The micro-scale elements may have a base length of less than 1 µm, 1 µm-1000 µm, 1 µm-100 µm, 10 µm-100 µm, 20 µm-100 µm, 40 µm-80 µm, 500 µm-1,000 µm, or 100 µm-1,000 µm, for example, 1 µm-60 µm, 10 µm-60 µm, 20 µm-60 µm, or 20 µm-40 µm. The micro-scale elements may have a base length to base width ratio of 6:1 to 1:1, for example 4:1 to 2:1 or 2:1 to 1:1.

The distal end of the micro-scale elements may be dimensioned to puncture or penetrate a layer of the target tissue. In particular, the distal end of the micro-scale elements may be dimensioned to have a radius of curvature small enough to puncture the target tissue with the applied penetration force. Sharpness of the micro-scale elements, for instance, an apex or vertex angle of the micro-scale elements, may be selected for the target tissue. The apex or vertex angle is shown in the exemplary embodiments of FIGS. 4-6 (labelled apex angle).

In general, a smaller apex or vertex angle may correspond with increased sharpness of the micro-scale element. A larger apex or vertex angle may correspond with decreased sharpness of the micro-scale element. In general, the apex or vertex angle may be as small as possible, for example, as permissible by tolerance of the manufacturing method. Exemplary apex and vertex angles include less than 15°, 15°-30°, 30°-45° and 45°-60°. In other embodiments, exemplary apex and vertex angles include 60°-90°, 90°-120° and 120°-180°. In some embodiments, the apex or vertex angle may have a rounded tip. Thus, the distal end of the micro-scale element may be rounded.

At least some of the micro-scale elements of the biocompatible adhesive may comprise at least one protrusion dimensioned to anchor the biocompatible adhesive to the target tissue. The at least one protrusion may be a physical element that extends from a surface of the micro-scale element. The at least one protrusion may be dimensioned to require lesser penetration force for entry of the micro-scale element than a removal force for extraction. For instance, the at least one protrusion may be dimensioned so as to facilitate entry into the target tissue and/or make extraction from the target tissue difficult.

A plurality of micro-scale elements of the biocompatible adhesive may have at least one protrusion. In some embodiments, substantially all of the micro-scale elements of the biocompatible adhesive comprise at least one protrusion. In other embodiments, a fraction of the micro-scale elements of the biocompatible adhesive comprise at least one protrusion, for example, 30%, 40%, 50%, 60%, 70%, 80%, or 90% of the micro-scale elements may comprise at least one protrusion.

The at least one protrusion may be multi-directional. In some embodiments, the micro-scale elements may be rotationally symmetric. For instance, the at least one protrusion may provide rotational symmetry to the micro-scale element. The at least one protrusion may be a radial protrusion, for example, a ring or other structure surrounding the base of the micro-scale element. In other embodiments, the micro-scale elements need not be rotationally symmetric. For instance, the at least one protrusion may be laterally located on one or more points of the micro-scale element (for example, as shown in FIG. 6). The at least one protrusion may be a lateral protrusion, for example, a barb or hook or other structure extending in one direction away from the base of the micro-scale element.

Figure 7:
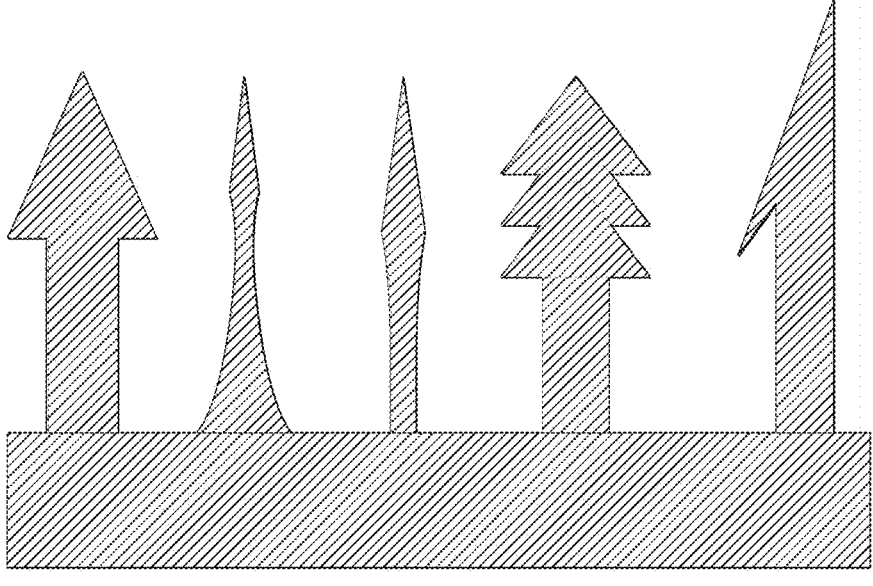
FIG. 7 is a schematic drawing of several embodiments of micro-scale elements.

The at least one protrusion may be positioned on a distal end of the micro-scale element. The at least one protrusion may be positioned along a base portion of the micro-scale element. Additionally, the micro-scale element may comprise at least one protrusion localized on a distal end and/or at least one protrusion localized along a base of the micro-scale element. Alternative exemplary embodiments of the micro-scale element are shown in FIG. 7.

The at least one protrusion may comprise a barb. As disclosed herein, an "barb" may refer to a projection angled away from the main point of the distal end of the micro-scale element. The barb may have a triangular cross-sectional area, for example, forming an arrowhead-shaped projection. The barb may have a cylindrical or rectangular cross-sectional area, for example, forming a rod-shaped projection. In some embodiments, the micro-scale elements may be barbed at the distal end. Thus, in some embodiments, the at least one protrusion may be barbed, for example, arrowhead-shaped or rod-shaped. In some embodiments, the micro-scale elements may comprise barbed, for example, arrowhead-shaped or rod-shaped, protrusions along the base of the micro-scale element.

Figure 8:
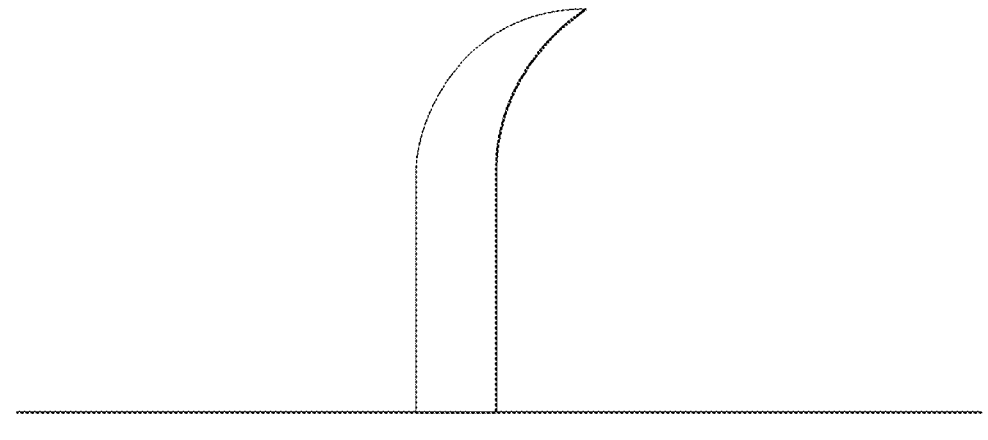
FIG. 8 is a schematic drawing of a micro-scale element, according to one embodiment.

The at least one protrusion may comprise a hook. As disclosed herein, a "hook" may refer to a projection that is curved or bent back or away at an angle from the direction of extension of the micro-scale element. The curved or bent projection may be elongated. The curved or bent projection may have a sharp end pointing in a direction away from the direction of extension of the micro-scale element. In some embodiments, the micro-scale elements may be hooked at the distal end. Thus, in some embodiments, the at least one protrusion may be hook-shaped. In some embodiments, the micro-scale elements may comprise hook-shaped protrusions along the base of the micro-scale element. Exemplary hook-shaped elements are shown in FIG. 6 and FIG. 8.

The at least one protrusion may comprise a ring. As disclosed herein, a "ring" may refer to a projection encircling the base of the micro-scale element. In some embodiments, the ring may be concentric with a base of the micro-scale element. In some embodiments, the at least one protrusion may be ring-shaped. The micro-scale element may comprise a plurality of concentric ring-shaped protrusions along the base of the micro-scale element. In some embodiments, the ring-shaped protrusion may be spiraled along the base of the micro-scale element. Thus, in some embodiments, the micro-scale elements may be screw shaped.

The micro-scale elements may have a protrusion length of less than 1 μm, 1 μm-100 μm, 10 μm-100 μm, 20 μm-100 μm, or 40 μm-80 μm, for example, 1 μm-60 μm, 10 μm-60 μm, 10 μm-20 μm, 10 μm-40 μm, or 20 μm-40 μm. The protrusion length may be defined from the proximal end of the protrusion adjacent to the base of the micro-scale element to the distal end of the protrusion, as shown in FIGS. 4-6. The micro-scale elements may have an element length to protrusion length ratio of 1:1 to 10:1, for example 1.1:1 to 6:1 or 2:1 to 6:1.

Protrusion undercut may be defined from the base width to the lateral extension of the protrusion, as shown in FIG. 4. In some embodiments, the protrusion undercut may be negative, as shown in FIG. 5.

Protrusion overhang may be defined as an excess length of the protrusion from a plane of the base length, as shown in FIG. 6. As described with respect to the hook-shaped protrusion above, the protrusion overhang may be a portion of the protrusion curved or bent back or away at an angle from the direction of extension of the micro-scale element.

FIG. 1 is a schematic drawing of one exemplary biocompatible adhesive 100. The biocompatible adhesive 100 of FIG. 1 includes a substrate 10, micro-scale elements 20 extending from a surface of the substrate 10, and arrowhead shaped protrusions 30 on a distal end of the micro-scale elements 20.

In some embodiments, the plurality of micro-scale elements may be substantially normal to the substrate. Thus, in some embodiments, the plurality of micro-scale elements may have a base angle of about 90°. The base angle may refer to an angle formed between the plane of the substrate and the extension of the micro-scale element from the substrate. The plane of the substrate may refer to a plane formed by the substrate in a flat position. The plane of the substrate may be determined at manufacturing. In general, the plane of the substrate may be determined when the substrate is in an extended conformation, for example, before the substrate adopts any flexed conformation. Exemplary base angles of about 90° are shown in FIGS. 4-6.

In some embodiments, the plurality of micro-scale elements may be angled. Thus, the plurality of micro-scale elements may have a base angle of less than about 90°. Base angles are identified in FIGS. 4-6. The base angle may be 15°-90°, for example, 30°-90°, 60°-90°, or 30°-60°. In certain embodiments, a fraction of the plurality of micro-scale elements may be normal to the substrate and a fraction of the micro-scale elements may be angled. For example, in some embodiments 30%, 40%, 50%, 60%, 70%, 80%, or 90% of the micro-scale elements may be angled.

The biocompatible adhesive disclosed herein may have a plurality of micro-scale elements. Recognizing that there may be variation in the geometries and dimensions of the plurality of micro-scale elements of the adhesive, the dimensions disclosed herein may generally refer to an average of the plurality of micro-scale elements. Furthermore, the micro-scale elements having the disclosed dimensions may be within tolerance of the disclosed dimensions, for example, within 5% or within 10% of the dimensions disclosed herein. In some embodiments, at least 40% of the micro-scale elements, for example, at least 50%, at least 60%, at least 70%, at least 80%, at least 90%, or at least 95% of the micro-scale elements may have the target geometries and dimensions.

The plurality of micro-scale elements may be arranged as an array of micro-scale elements extending from the surface of the substrate. The array may be a grid of micro-scale elements arranged in rows and columns. In some embodiments, the rows and/or columns may be aligned. In some embodiments, the rows and/or columns may be offset. The density of micro-scale elements may be from 100-10,000 micro-scale elements per cm2 of the substrate surface area, for example, 100-200, 200-500, 500-750, 750-1,000, 1,000-2,000, 1,000-5,000, 5,000-7,500, or 5,000-10,000 micro-scale elements per cm2 of the substrate area.

The plurality of micro-scale elements arranged as an array may each be spaced apart by 50 μm-500 μm, for example, by 50 μm-100 μm, 100 μm-200 μm, 100 μm-300 μm, 300 μm-400 μm, or 300 μm-500 μm. The micro-scale elements arranged as an array may be substantially equally spaced apart. The micro-scale elements may be differentially spaced apart, for example, arranged in a plurality of more compact regions. The more compact regions may be, for example, smaller grids or rows of micro-scale elements.

A greater density of micro-scale elements may provide a greater adhesion force of the biocompatible adhesive and require a greater removal force for removal of the biocompatible adhesive. The density and/or other properties of the biocompatible adhesive (e.g., size) may be selected based on a desired adhesion and/or removal force of the biocompatible device to or from the target tissue. While the adhesion and/or removal force may generally be as great as necessary for the selected application or target tissue, in some embodiments, the adhesion and/or removal force of the biocompatible adhesive may be 0.5 N/cm2-5.0 N/cm2, for example, at least about 0.5 N/cm2, 1.0 N/cm2, 1.5 N/cm2, 2.0 N/cm2, 2.5 N/cm2, 3.0 N/cm2, 3.5 N/cm2, 4.0 N/cm2, 4.5 N/cm2, or 5.0 N/cm2.

In some embodiments, the biocompatible adhesive may be permanently attachable to the target tissue. Permanent attachment may generally refer to an attachment that is removable only with specialized labor and/or tools, for example, surgically removable attachment. In some embodiments, the biocompatible adhesive may be reversibly attachable to the target tissue. Reversible attachment may generally refer to an attachment that is removable with unskilled labor and, optionally, without the use of tools. The biocompatible adhesive, for example, the reversibly attachable biocompatible adhesive, may cause minimal damage to the target tissue upon removal. In some embodiments, the reversibly attachable adhesive may be re-attached after removal. In general, a permanently attachable and reversibly attachable adhesive do not substantially detach spontaneously, for example, without manual intervention.

The micro-scale elements and protrusions of the biocompatible adhesives disclosed herein may provide rapid adhesion. For instance, anchoring the biocompatible adhesive to the target tissue generally provides substantially simultaneous attachment of the micro-scale elements of the biocompatible adhesive to the target tissue. Anchoring the biocompatible adhesive may be effectuated immediately upon penetration of the layer of the target tissue. Thus, the micro-scale elements and protrusions generally do not require a period of equilibration after application for anchoring to the target tissue. Moreover, the biocompatible adhesive as an "out-of-the-box" product may be effective for immediate attachment by comprising micro-scale elements dimensioned to anchor the target tissue. Such embodiments allow rapid adhesion with the biocompatible adhesives disclosed herein, significantly reducing procedure times and significantly facilitating attachment and wound treatment in the field.

Figure 2A:
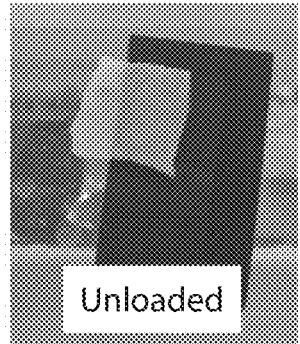
FIG. 2A is a photograph of an unloaded biocompatible adhesive, according to one embodiment.
Figure 2B:
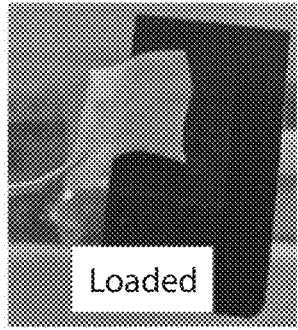
FIG. 2 B is a photograph of a loaded biocompatible adhesive, according to one embodiment.
Figure 3A:
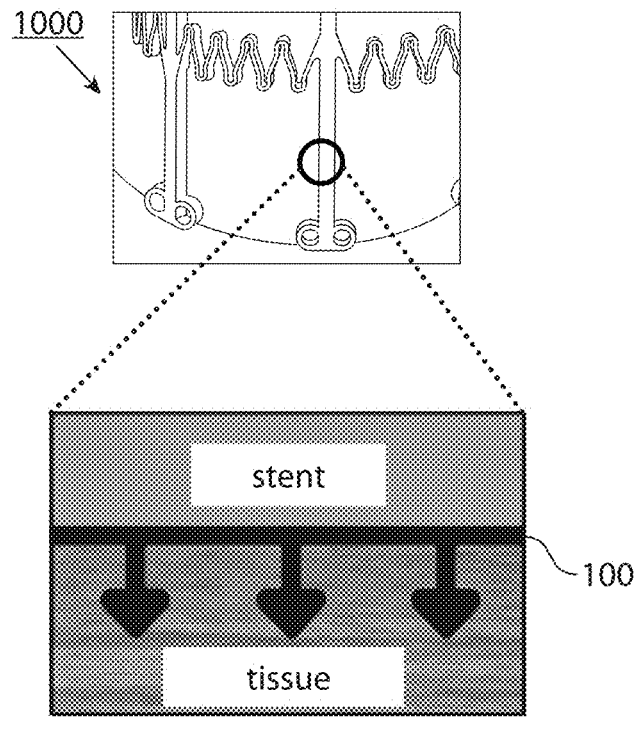
FIG. 3 A is a schematic drawing of a portion of a medical device assembly, according to one embodiment.
Figure 3B:
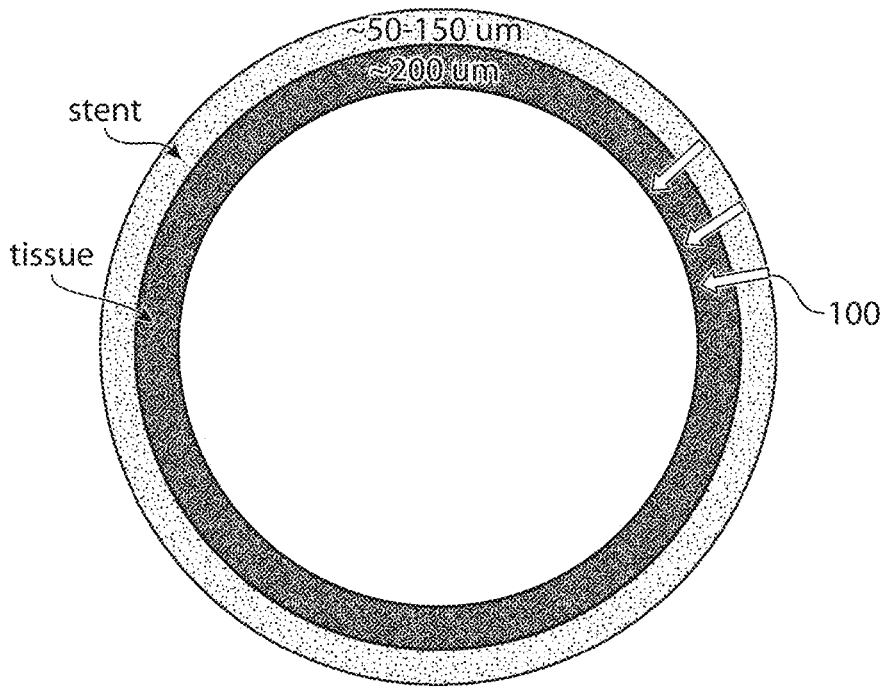
Figure 3C:
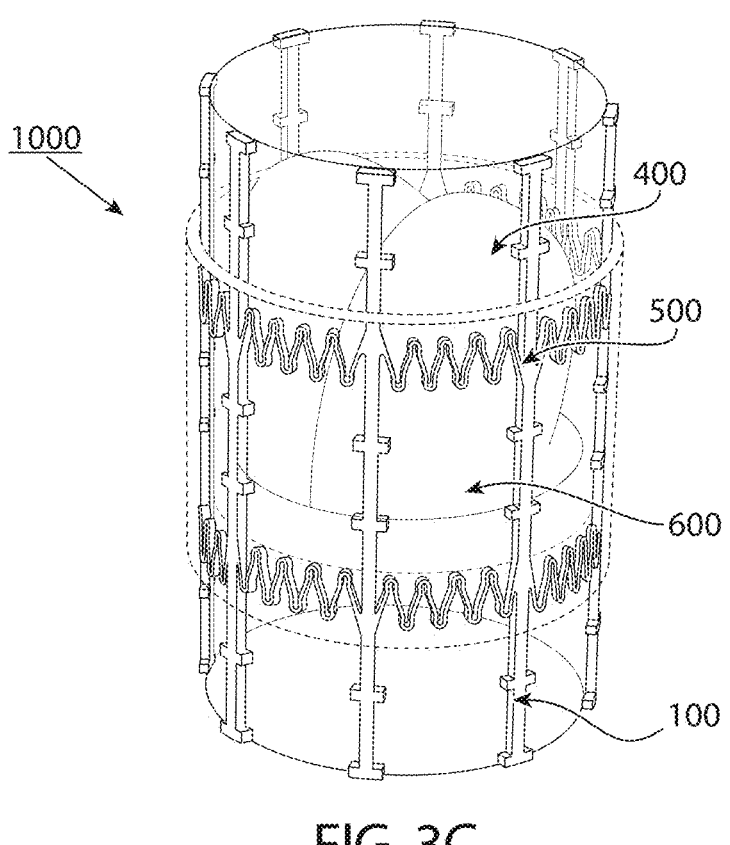
Figure 3D:
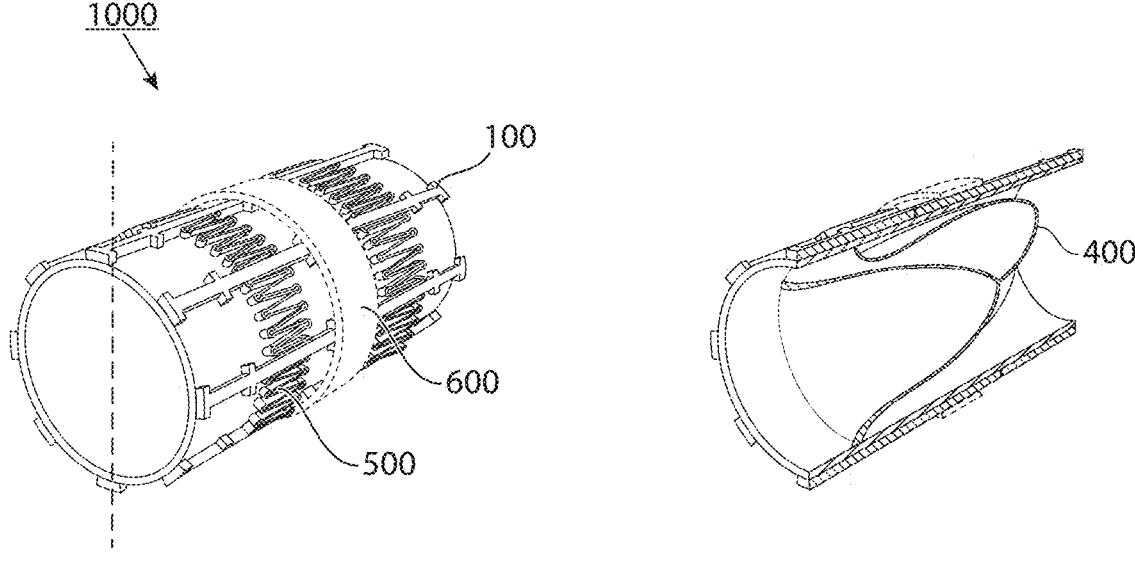

FIGS. 2 A-2 B are photographs of exemplary biocompatible adhesives. As shown in the photograph of FIG. 2 A, a biocompatible adhesive in an "unloaded" state may not be anchored to the target tissue. As shown in the photograph of FIG. 2 B, a biocompatible adhesive in a "loaded" state may be anchored to the target tissue. Anchoring the biocompatible adhesive may be effectuated immediately upon penetration of the layer of the target tissue. For instance, applying a small pressure to the biocompatible adhesive may anchor the biocompatible adhesive to the target tissue.

The biocompatible adhesive or a component thereof may be formed of a polymeric material. For example, in some embodiments, the substrate or a portion thereof may be formed of a polymeric material. In some embodiments, the micro-scale elements or a portion thereof may be formed of a polymeric material. Exemplary biocompatible polymers include, for example, polyurethanes, silicones, poly(2-methoxyethlacrylate), BioSpan® segmented polyether polyurethane (SPU) (distributed by DSM, Heerlen, Netherlands), PurSil® thermoplastic silicone polyether polyurethane (TSPU) (distributed by DSM, Heerlen, Netherlands), and Onyx@ ethylene vinyl alcohol (EVOH) (distributed by MicroTherapeutics, Inc., Irvine, Calif.). The material may be selected from polymeric materials having differing durometers.

In some embodiments, the biocompatible adhesive or component may be formed of a rigid or semi-rigid polymeric material. The rigid or semi-rigid polymeric material may be selected to provide structural support. In some embodiments, the biocompatible adhesive or component thereof may be formed of a flexible polymeric material. The flexible polymeric material may be selected to be compatible with target tissue flexibility and movement.

The biocompatible adhesive or a component thereof may be formed of a metal material, for example, a metal or metal alloy. For example, in some embodiments, the substrate or a portion thereof may be formed of a metal material. In some embodiments, the micro-scale elements or a portion thereof may be formed of a metal material. Exemplary biocompatible metal materials include stainless steel, cobalt-chrome alloy, titanium, and nickel-titanium alloy (nitinol). Other metals, such as gold, platinum, silver, aluminum, iridium, tantalum, and tungsten may be used. The metal material may be a rigid or semi-rigid material. In some embodiments, the metal material may be selected to have a desired rigidity, for example, to provide structural support.

In some embodiments, the biocompatible adhesive or component may be formed of a rigid or semi-rigid metal material. The rigid or semi-rigid metal material may be selected to provide structural support. In some embodiments, the biocompatible adhesive or component thereof may be formed of a pliable metal material. The pliable metal material may be selected to be compatible with target tissue flexibility and movement.

In some embodiments, the biocompatible adhesive may be formed of a combination of materials. For instance, the biocompatible adhesive may be formed of two or more polymeric materials. The biocompatible adhesive may be formed of one or more metal and polymeric materials. For instance, the substrate may be formed of a first material and the micro-scale elements may be formed of a second material. In some embodiments, the substrate may be formed of a more flexible material and the micro-scale elements may be formed of a more rigid or semi-rigid material. For example, in at least some exemplary embodiments, the substrate may be formed of a flexible polymeric material and the micro-scale elements may be formed of a rigid or semi-rigid polymeric material or a metal material. In certain embodiments, the substrate and/or micro-scale elements may comprise a rigid or semi-rigid core. The substrate and/or micro-scale elements may comprise a flexible outer layer. In one exemplary embodiment, the substrate may comprise a flexible material and the micro-scale elements may comprise a rigid or semi-rigid core with a flexible outer layer. The flexible outer layer may form the one or more protrusions.

Thus, in certain embodiments, the substrate may be formed of a first material and the micro-scale elements may be formed of a second material. In some embodiments, the substrate may comprise portions formed of a first material and portions formed of a second material and/or the micro-scale elements may comprise portions formed of a first material and portions formed of a second material. For instance, the micro-scale elements may comprise a core formed of a first material and an outer layer formed of a second material. In certain exemplary embodiments, the micro-scale elements may comprise one or more protrusions formed of a second material. The materials may be independently selected to be a polymeric material, a variety of polymeric materials (for example, a first polymeric material and a second polymeric material), a metal material, and/or a variety of metal materials (for example, a first metal material and a second metal material). The materials may be independently selected to provide desired rigidity or flexibility.

While the micro-scale elements are generally dimensioned to anchor the biocompatible adhesive to the target tissue substantially simultaneously upon attachment, the biocompatible adhesive and/or the substrate may be formed of a material capable of expansion over time. In particular, for extended use or permanent use of the biocompatible adhesives, the material may be selected to provide expansion proportional to the growth rate of the target tissue. Thus, the biocompatible adhesive may remain attached even as the target tissue of the subject grows. Additionally, for dynamic tissues, such as cardiac, pulmonary, and muscle tissues, the material may be selected to provide reversible expansion with movement of the target tissue. Thus, the biocompatible adhesive may remain attached with expansion and contraction of the target tissue.

The micro-scale elements may be formed of a material and/or be dimensioned to reduce breakage from the substrate during use. Thus, the material and/or dimensions (for example, base width and length dimensions) may be selected based on the target tissue. Certain target tissues that have more movement may require more flexible micro-scale elements. Certain target tissues that require greater penetration force may require more rigid micro-scale elements. In certain embodiments, at least 50%, at least 60%, at least 70%, at least 80%, at least 90%, at least 95%, or at least 99% of the micro-scale elements may remain attached to the substrate after a pre-determined period of use, for example, after 24 hours, after 48 hours, after 1 week, after 1 month, or after 1 year of use.

In certain embodiments, the biocompatible adhesive or a component thereof may be sterile or substantially sterile. For example, the micro-scale elements may be sterile or substantially sterile. The sterile adhesive or components may be free or substantially free of microorganisms, for example, pathogenic microorganisms. In some embodiments, the adhesive or component may be characterized as sterile in accordance with the Association of Surgical Technologists (AST) guidelines.

In certain embodiments, the biocompatible adhesive may comprise a therapeutically active agent. The therapeutically active agent may be an anti-inflammatory, antimicrobial, or antiseptic agent. Exemplary anti-inflammatory agents include topical anti-inflammatory agents, such as ibuprofen, diclofenac, felbinac, ketoprofen, piroxicam, dexamethasone, and others. Antimicrobial and antiseptic agents may inhibit the growth or reproduction or destroy microorganisms such as fungi, viruses, bacteria, and combinations thereof. In particular, the antimicrobial or antiseptic agent may inhibit the growth or reproduction or destroy pathogenic microorganisms. Antimicrobial and antiseptic agents may additionally prevent or treat an infection by a pathogenic microorganism. Exemplary antimicrobial agents include mupirocin, fusidic acid, neomycin, bacitracin, polymyxins, retapamulin, ebselen, and antimicrobial peptides, such as PXL150 and others. Exemplary antiseptic agents include biocides, such as chlorhexidine, trisclosan, povidone-iodine, and alcohol-based biocides. It should be noted that several therapeutic agents may have more than one effect, for example, more than one of an anti-inflammatory, antimicrobial, and antiseptic effect. In some embodiments, the therapeutic agent may be formulated to provide a prophylactic treatment.

The therapeutically active agent may be coated on a surface of the biocompatible adhesive, for example, on a surface of at least some of the plurality of micro-scale elements. The therapeutically active coating may be formulated for immediate release. The therapeutically active coating may be formulated for extended release or delayed release. In general, the therapeutically active coating may be formulated to provide a local effect, for example, an effect at the target tissue. However, in certain embodiments, the therapeutically active coating may be formulated to provide a systemic effect, for example, an effect at a tissue other than the target tissue.

In some embodiments, the biocompatible adhesive may comprise a deployable element configured to deliver the therapeutically active agent to the target tissue. The deployable element may comprise, for example, a releasable micro-scale element or a releasable protrusion of a micro-scale element. The deployable element may comprise microcapsules. The deployable element may be formulated for immediate release. The deployable element may be formulated for extended release or delayed release. The deployable element may be formulated to provide a local effect, for example, an effect at the target tissue. The deployable element may be formulated to provide a system effect, for example, an effect at a tissue other than the target tissue. In some embodiments, the deployable element may be configured to migrate to a tissue other than the target tissue.

The biocompatible adhesives described herein may be manufactured by a number of different micro-scale product manufacturing methods. Exemplary manufacturing methods include injection molding, e.g., polymer molding or metal molding, additive manufacturing, metal cutting, e.g., laser cutting, plasma cutting, water jetting, microfabrication lithography, metal etching, or others. The manufacturing method may be selected based on the material of the biocompatible adhesive and/or the material of the micro-scale elements. In one exemplary embodiment, the biocompatible adhesive may be manufactured by bi-layer injection molding. For instance, the micro-scale elements may be molded from a first layer of the mold and the at least one protrusion may be molded from a second layer of the mold. The geometries of the bi-layer mold may be selected to reduce breakage of the protrusions from the micro-scale elements upon removal. A tri-layer mold may be used, for example, to manufacture a double-sided biocompatible adhesive. Thus, in some embodiments, the biocompatible adhesive may be manufactured with a two- or three-step injection molding technique.

In accordance with another aspect, there is provided a medical device assembly comprising the biocompatible adhesive. The biocompatible adhesive may be employed to facilitate attachment of the medical device assembly to a target tissue. In some embodiments, the biocompatible adhesive may be coupled to a surface of the medical device assembly and positioned to attach the medical device assembly to the target tissue. The biocompatible adhesive may be coupled to an exterior surface of the medical device assembly. An exterior surface of the medical device assembly includes any surface that may be contacted by a foreign material, such as an external wall of the device or an internal wall of a tubular structure.

The medical device assembly may comprise a plurality of components. In some embodiments, the medical device assembly may comprise a biocompatible adhesive coupling a first component of the medical device assembly to a second component of the medical device assembly. The first component and the second component may have similar properties, for example, may be formed of materials having similar properties. The first component and the second component may have different properties, for example, may be formed of materials having different properties.

The medical device assembly may be any medical device, such as a diagnostic, therapeutic, or monitoring device. The medical device assembly may be a bioprosthetic device, for example, integrating bioprosthetic tissue with live tissue. The medical device assembly may be a prosthetic device, for example, integrating biocompatible materials with bioprosthetic or live tissue. The medical device assembly may be a catheter or tube configured to be integrated with a biological lumen. The medical device assembly may be an orthopedic or implant material configured to be integrated with hard tissue, such as bone or cartilage.

In certain exemplary embodiments, the medical device assembly may be a stent. Exemplary stents are described in International Application Publication No. WO2019/033026 titled "Growth-Adaptive Expandable Stent," filed Aug. 10, 2018, incorporated herein by reference in its entirety for all purposes. The biocompatible adhesive may be coupled to a surface of any one or more component of the stent.

In certain exemplary embodiments, the medical device assembly may be a prosthetic heart valve. Exemplary prosthetic heart valves are described in International Application Publication No. WO2019/094342 titled "Segmented, Growth-Accommodating, Artificial Valve," filed Nov. 5, 2018, incorporated herein by reference in its entirety for all purposes. The biocompatible adhesive may be coupled to a surface of any one or more component of the prosthetic heart valve.

One exemplary medical device is a prosthetic heart valve. In some embodiments, the prosthetic heart valve may be a pediatric heart valve. In some embodiments, target tissue may be a bioprosthetic tissue, for example, the bioprosthetic tissue may be a valve of the prosthetic heart valve. The bioprosthetic tissue may be a vein, for example, a vein from an allogeneic or xenogeneic donor. Thus, the biocompatible adhesive may be designed to anchor a vein. Additionally, in such exemplary embodiments, a first component of the heart valve may be a suture skirt and a second component may be a stent. The prosthetic heart valve may comprise a biocompatible adhesive coupling the suture skirt to the stent.

The medical device assembly may be formed of a biocompatible material. In some embodiments, the medical device assembly may be formed of a polymeric material or coated in a polymeric material. The biocompatible adhesive may have micro-scale elements having a length selected to puncture or penetrate a target material, for example, polymeric layer, of the medical device assembly. The micro-scale elements may have at least one protrusion dimensioned to anchor the biocompatible adhesive to the target material, for example, polymeric surface of the medical device assembly. In certain embodiments, a double-sided biocompatible adhesive may have micro-scale elements and/or protrusions designed to couple a first component of the medical device assembly to a second component of the medical device assembly. For instance, a first side of the biocompatible adhesive may be designed to anchor the first component and a second side of the biocompatible adhesive may be designed to anchor the second component.

The biocompatible adhesive may be coupled to a surface of the medical device assembly. In some embodiments, the biocompatible adhesive may be formed as a coating or over-mold of the medical device assembly component. In some embodiments, the biocompatible adhesive may be mechanically coupled to the medical device assembly. For example, the biocompatible adhesive may be fixed to the medical device assembly component with sutures. In some embodiments, the biocompatible adhesive may be coupled to the medical device assembly with a chemical or conventional adhesive. In some embodiments, the biocompatible adhesive may be coupled to the medical device assembly by an adhesive side of the biocompatible adhesive. For instance, a double-sided biocompatible adhesive may be used. The adhesive side configured to contact the medical device assembly may be engineered to anchor a target material of the medical device assembly.

In some embodiments, the medical device assembly may be implantable. Thus, the biocompatible adhesive may be selected to penetrate and anchor an internal target tissue. In other embodiments, the medical device assembly may be external. Thus, the biocompatible adhesive may be selected to penetrate and anchor an external target tissue. In yet other embodiments, the medical device assembly may be partially implantable. Thus, the medical device assembly may be configured to contact more than one type of tissue. The medical device assembly may comprise a plurality of biocompatible adhesives, each selected to penetrate and anchor a corresponding target tissue.

FIG. 5 is a schematic drawing of a portion of a medical device assembly comprising the biocompatible adhesive. As shown in the exemplary embodiment of FIG. 5, the biocompatible adhesive may be coupled to a surface of the medical device assembly such as a stent. The biocompatible adhesive may be positioned to attach the medical device assembly to the target tissue.

In accordance with another aspect, there is provided a method of facilitating attachment of a medical device assembly to a target tissue. The method may comprise providing a biocompatible adhesive, as described herein. The method may comprise providing instructions to couple the biocompatible adhesive to a surface of the medical device assembly, positioned to attach the medical device assembly to the target tissue. In certain embodiments, the method may comprise coupling the biocompatible adhesive to the surface.

In some embodiments, the method may comprise providing more than one biocompatible adhesive. For instance, a first biocompatible adhesive may be provided to couple the medical device assembly to the target tissue. A second biocompatible adhesive may be provided to couple a first component of the medical device assembly to a second component of the medical device assembly. Thus, the method may comprise providing instructions to couple the first component of the medical device assembly to the second component of the medical device assembly. In certain embodiments, the method may comprise coupling the first component of the medical device assembly to the second component of the medical device assembly.

In accordance with yet another aspect, there is provided a method of treating a wound on a target tissue of a subject. The wound may be any insult or injury to the target tissue. For instance, the wound may be a laceration or puncture, the wound may be a burn or freeze, the wound may be a contusion, the wound may be a welt or other local inflammation, or other insult or injury that benefits from covering and/or closure. One exemplary wound treatment is anastomosis, which includes connecting edges of severed blood vessels. The wound may be on an external target tissue. The wound may be on an internal target tissue.

As used herein, treatment of a wound refers to reducing the severity of the wound, compared to a similar but untreated target tissue. Treatment can refer to halting, slowing, or reversing the progression of the wound, compared to a similar but untreated target tissue. In certain embodiments, treatment may refer to wound closure, for example, closure of a laceration or puncture. Wound closure may be considered bringing together wound edges. In certain embodiments, wound closure may not require epithelization. In other embodiments, wound closure may include partial epithelization, or complete epithelization of the target tissue. Treatment may refer to reducing inflammation or inhibiting an increase of inflammation of the target tissue. Treatment may refer to protection from a microbial infection or reduction or elimination of a microbial infection.

The method may comprise providing a biocompatible adhesive, as disclosed herein. The biocompatible adhesive may me designed to anchor the target tissue. The biocompatible adhesive may have material properties, e.g., flexibility or rigidity, designed to be compatible with the target tissue. The biocompatible adhesive may comprise a therapeutically active agent, as previously described. Thus, the biocompatible adhesive may be configured to deliver a therapeutically active agent locally or systemically.

The method may comprise providing instructions to anchor the biocompatible adhesive to the target tissue thereby treating the wound. The biocompatible adhesive may be anchored to surround the wound and/or covering the wound. In some embodiments, for example, to facilitate treatment of acute or healable wounds, the biocompatible adhesive may be reversibly attachable to the target tissue and optionally biodegradable. In some embodiments, for example, to facilitate treatment of permanent or chronic wounds, the biocompatible adhesive may be permanently attachable to the target tissue and optionally non-biodegradable.

In certain embodiments, the method may comprise anchoring the biocompatible adhesive to the target tissue. In some embodiments, the method may comprise anchoring the biocompatible adhesive to the target tissue on opposite sides of the wound, such that the biocompatible adhesive surrounds and/or covers the wound. In general, anchoring the biocompatible adhesive to the target tissue may provide substantially simultaneous attachment of the biocompatible adhesive to the target tissue. Rapid adhesion may facilitate treatment of life-threatening wounds with minimal equipment and low skill.

In certain embodiments, the micro-scale elements of the biocompatible adhesive may have a length selected to puncture or penetrate more than one layer of the target tissue, for example, an external or exposed layer and one or more internal layers of the target tissue. For instance, in certain embodiments, delivery of a therapeutic agent to one or more internal layer of the target tissue may be desirable. The micro-scale elements may have a length selected to deliver the therapeutic agent to the desired layer of the target tissue.

EXAMPLES

The function and advantages of these and other embodiments can be better understood from the following example. This example is intended to be illustrative in nature and is not considered to be limiting the scope of the invention.

Prophetic Example: Prosthetic Pediatric Heart Valve

An adaptable and expandable prosthetic pediatric heart valve will be manufactured with the biocompatible adhesive as disclosed herein. The device will be designed for implantation during open heart surgery in early life. A typical valve replacement device would be sutured in place at the implantation site via the suture skirt. The device will be designed to expand passively as the surrounding tissue grows due to the spring behavior of the stent.

Instead of suturing the outer wall of the bioprosthetic valve conduit to the stent, the manufactured device will utilize the biocompatible adhesive for rapid, low skill, and reliable adhesion of the valve to the stent (FIGS. 3 A-3 D). Thus, the biocompatible adhesive would allow manufacturing of the small sized pediatric device with minimal suturing, which is the conventional method for attachment of bioprosthetic heart valves to stents.

Referring specifically to FIGS. 3 A-3 B, FIG. 3 A shows an exemplary medical device assembly 1000 and a magnified portion of the medical device assembly 1000 showing a stent and target tissue. Biocompatible adhesive 100 is positioned to attach the stent to the target tissue. As shown in FIG. 3 B, the stent may have a thickness of about 50 μm to about 150 μm. The target tissue, in this example a vein or blood vessel wall, may have a thickness of about 200 μm. The biocompatible adhesive 100 may have a projection length selected to puncture the target tissue but not fully penetrate into the lumen, for example, of less than 200 μm.

Referring specifically to FIGS. 3 C-3 D, several views of the exemplary medical device assembly 1000 are shown. The medical device assembly 1000 comprises expandable valve 400, growth-adaptive stent 500, suture skirt 600, and biocompatible adhesive 100 integrated into a component of the medical device assembly.

Attachment of the bioprosthetic valve to the growth adaptive stent may be viewed as a manufacturing/assembly step performed to create the device. In certain instances, the fully integrated device would be provided for clinical use as a final product. In other instances, the method may involve custom assembly by the surgeon in the operating room.

The pediatric heart valve will be manufactured with a stent coating or covering formed of the biocompatible adhesive, with micro-scale elements that will penetrate (but not fully puncture through) the outer wall of the valve conduit, forming a permanent mechanical adhesion. The biocompatible adhesive will be non-degradable and remain in the tissue, securing the tissue valve to the stent permanently. The biocompatible adhesive will be formed of a polymer such as polyurethane or silicone, and/or metal microstructures. The length of the micro-scale elements will be selected such that they will not fully puncture the bioprosthetic tissue wall, which could cause leakage and subsequent failure of the device.

All biocompatible adhesive components will be protected from contacting the blood. The biocompatible adhesive components will be positioned on a tissue contacting surface of the pediatric heart valve including suture skirt, sutures, and bare surfaces of the stent.

The attachment of the biocompatible adhesive to the stent will be largely dependent on the process developed to fabricate the structures. One approach (with a polymer-based microstructure) is to coat or over-mold the stent with the biocompatible adhesive structure. Another approach (with a metal-based microstructure) is to glue or weld an etched foil onto the stent. Alternatively, a sheet of the biocompatible adhesive may be fabricated and wrapped around the stent and attached. The biocompatible adhesive may be attached to the stent with sutures, adhesives, or similar mechanisms. The biocompatible adhesive may be used in conjunction with conventional sutures, but still utilizing significantly fewer sutures than currently required to manufacture bioprosthetic valves.

Example: Biocompatible Adhesives

Figure 9:
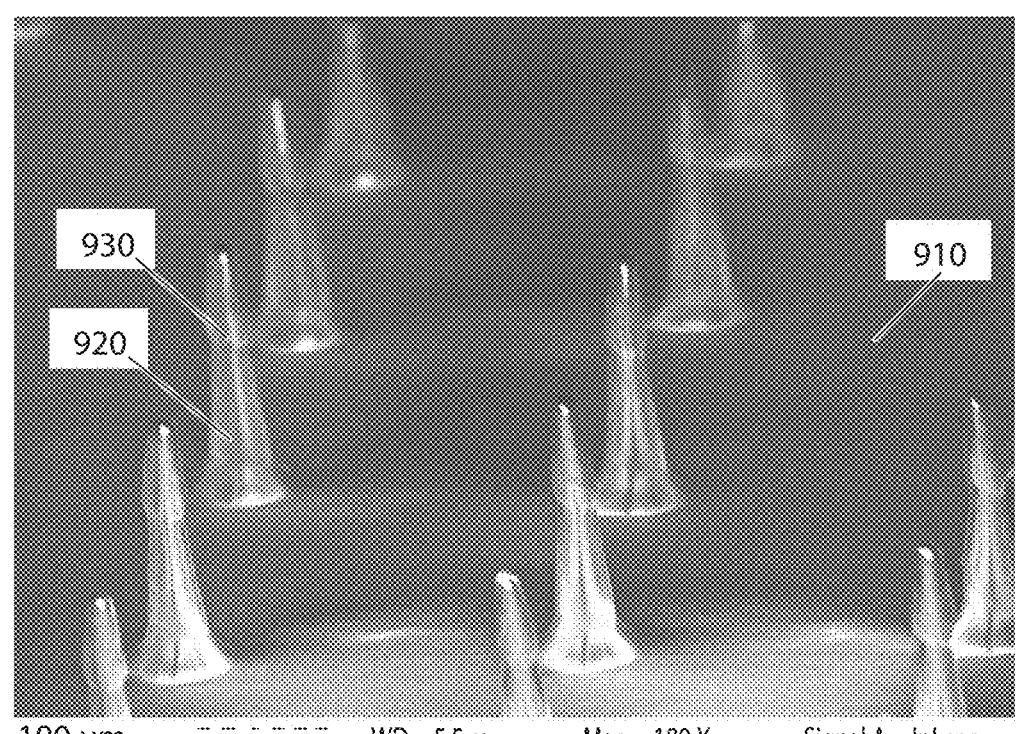
FIG. 9 is a magnified image of a plurality of micro-scale elements, according to one embodiment.
Figure 10:
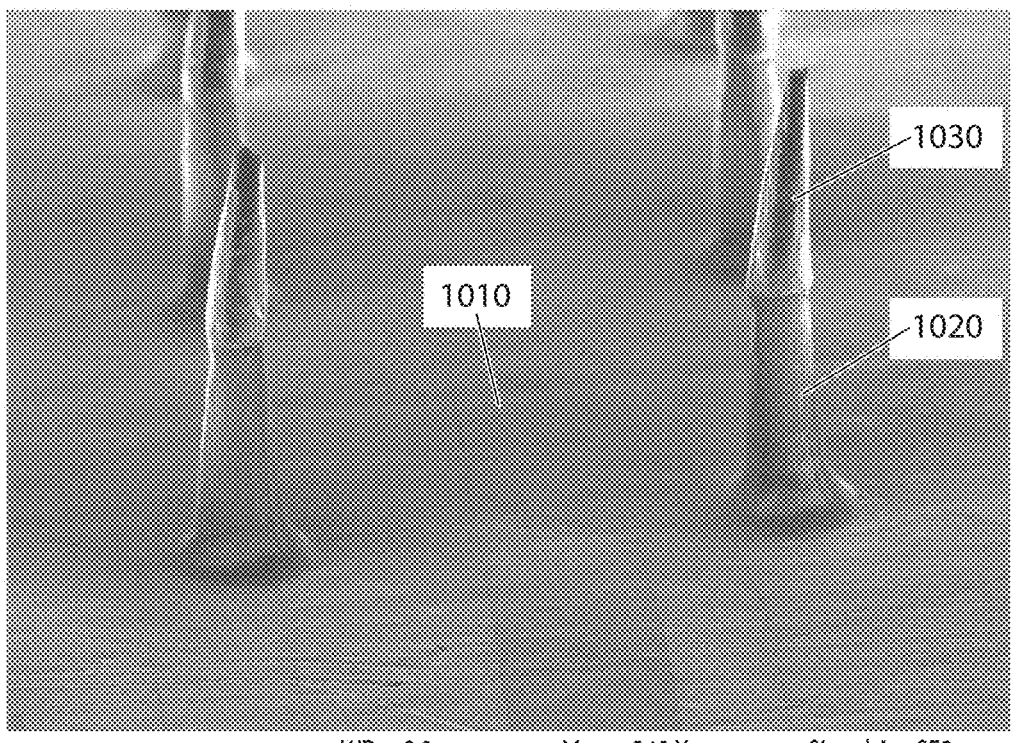
FIG. 10 is a magnified image of a plurality of micro-scale elements, according to one embodiment.
Figure 11:
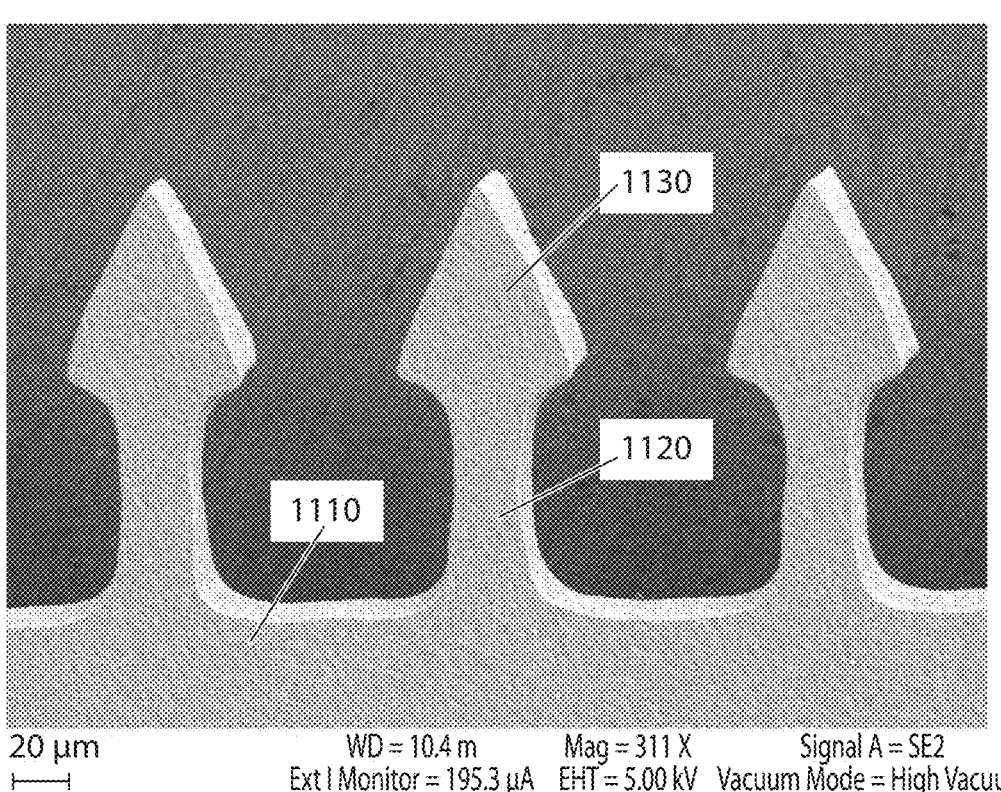
FIG. 11 is a magnified image of a plurality of micro-scale elements, according to one embodiment.
Figure 12:
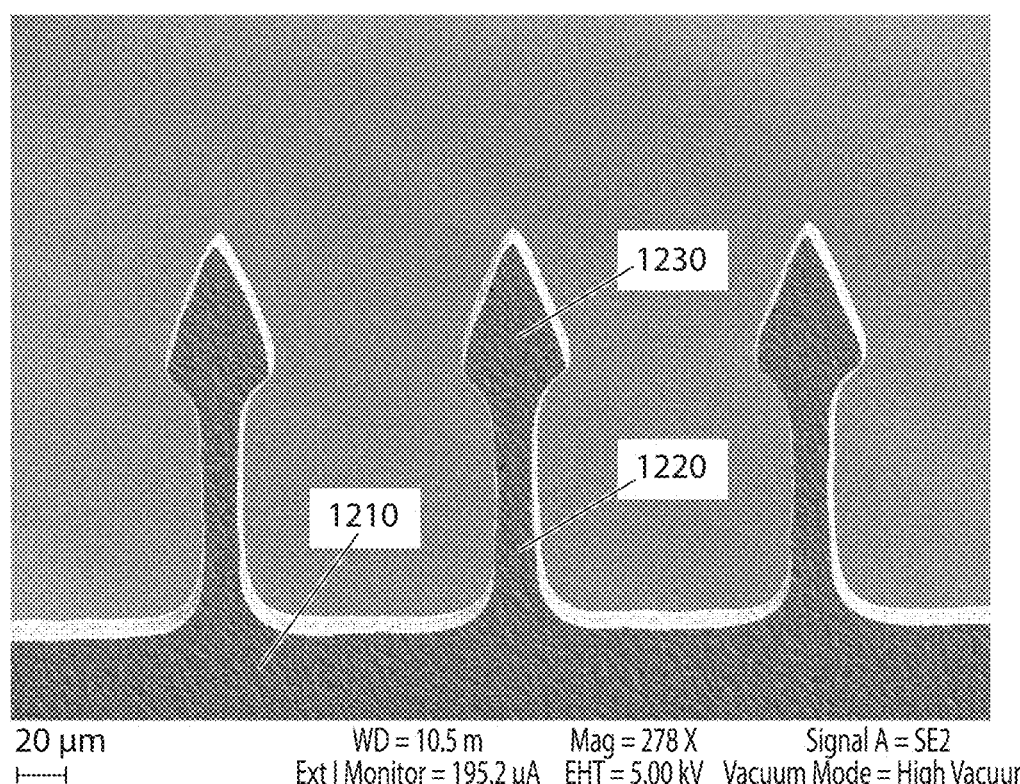
FIG. 12 is a magnified image of a plurality of micro-scale elements, according to one embodiment.

Biocompatible adhesives as described herein were produced. Magnified images of the biocompatible adhesives are shown in FIGS. 9-12. FIG. 9 is a magnified image (189× magnification) showing a top profile view of a substrate 910, micro-scale elements 920, and protrusions 930. The protrusions 930 are arrowhead-shaped protrusions. FIG. 10 is a magnified image (240× magnification) showing a top profile view of substrate 1010, micro-scale elements 1020, and protrusions 1030. Protrusions 1030 are hook-shaped protrusions. FIG. 11 is a magnified image (311× magnification) showing a side view of a substrate 1110, micro-scale elements 1120, and protrusions 1130. Protrusions 1130 are arrowhead-shaped protrusions. FIG. 12 is a magnified image (278× magnification) showing a side view of a substrate 1210, micro-scale elements 1220, and protrusions 1230. Protrusions 1230 are arrowhead-shaped protrusions.

Figure 13:
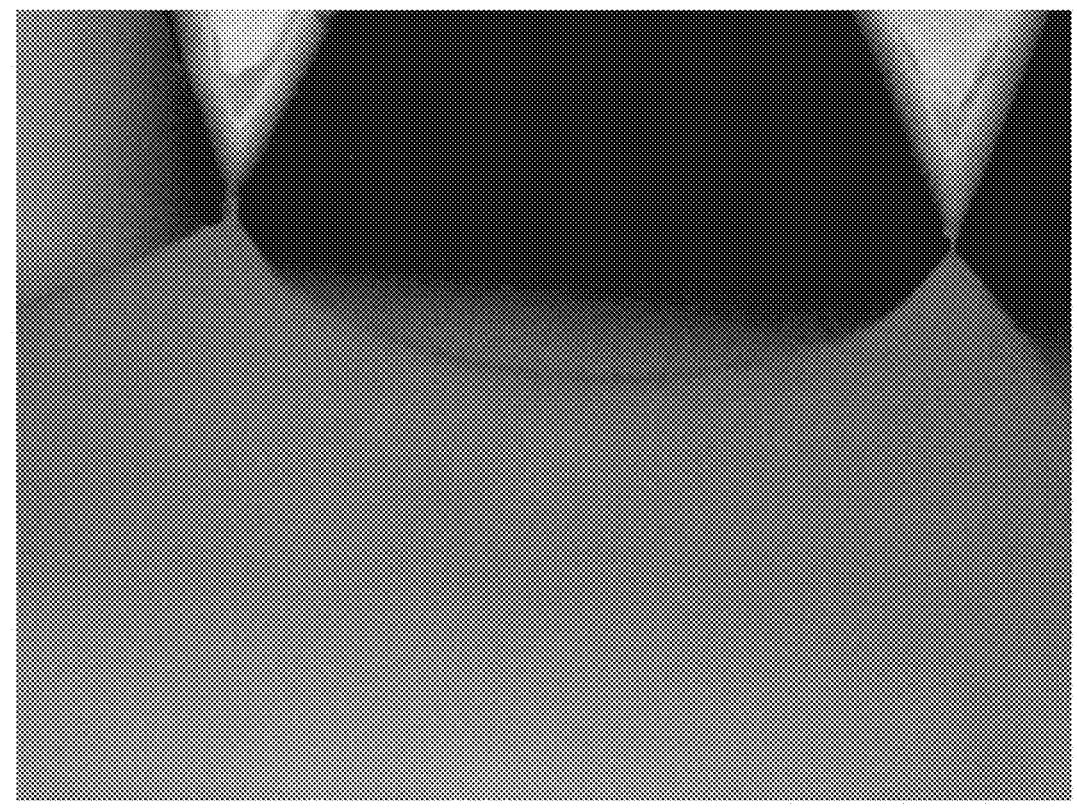
FIG. 13 is a magnified image of a plurality of micro-scale elements attached to a target material, according to one embodiment.

Adhesion of the exemplary biocompatible adhesives was tested. A magnified image of a biocompatible adhesive being detached from a target material is shown in FIG. 13. As shown in FIG. 13, the micro-scale elements of the biocompatible adhesive form an attachment with the target material. Briefly, adhesion of two microscale elements as shown in FIG. 12 was tested against a section of human femoral vein tissue as the target tissue. The human femoral vein tissue was fixed to a test stage outside the field of view of the image. The micro-scale elements were controllably pushed into the tissue sample to a known depth and then retracted, resulting in a pulling up of the tissue as the elements resisted separation. The micro-scale elements were shown to have been attached with adequate adhesion to stretch the tissue into a tent-like structure. After the image of FIG. 13 was taken, the micro-scale elements were further retracted and released from the target tissue. The target tissue returned to its original state. Accordingly, the biocompatible adhesives described herein effectively adhere to target tissues and release without causing substantial damage to the target tissue.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure and are intended to be within the scope of the invention. Accordingly, the foregoing description and drawings are by way of example only.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed.

Now referring to FIGS. 14-17, most microneedles are fabricated using cleanroom-based approaches which are well-suited to produce thousands of microchips with billions of transistors, but which are not economically transferable to applications with unusual topography and/or large surface areas. The process to make a barbed microstructure design using traditional photolithography processes requires multiple, complex steps in a cleanroom facility. Cleanroom based methods, which are typically applicable to microneedle fabrication, offer the potential for mass production, but such methods may also be optimized for making planar electronics devices. Because microneedles are non-planar and not electronic, microneedle fabrication may require specific processes and materials, increasing development costs and precluding fabrication in standard foundries where one can take advantage of low-cost, scalable production.

By leveraging microneedles, the adhesion may be enhanced via rationally designed mechanical interlocking with tissue. Specifically, processes for a metal microstructure, as well as a polymer microstructure, are described herein.

Figure 14:
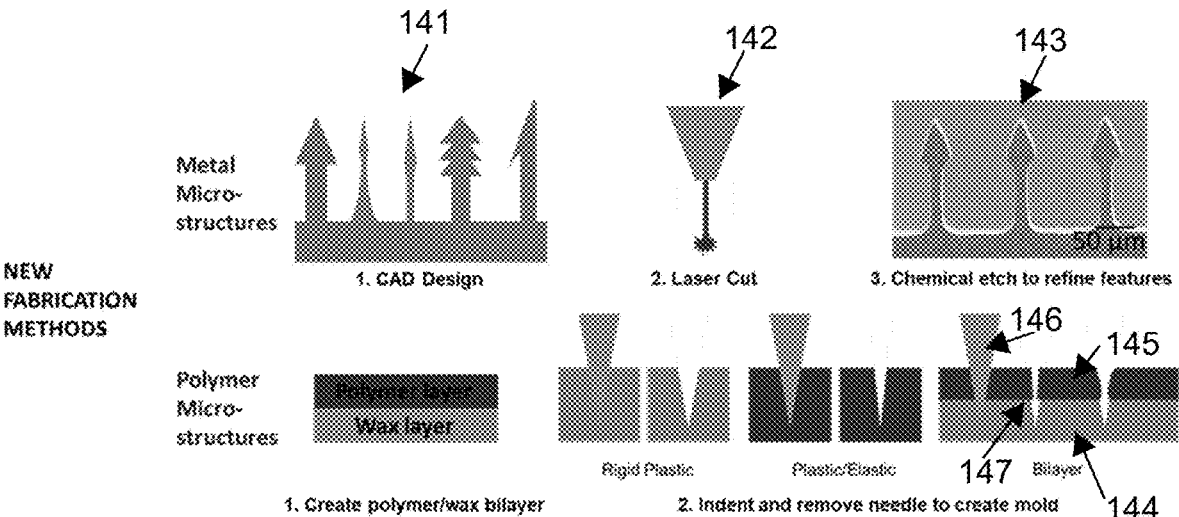
FIG. 14 is a schematic drawing of methods for fabricating metal or polymer microstructures.

In one example with respect to the metal microstructure, a method is therefore provided for fabricating metal microstructures. The method may be cleanroom-free. As shown in FIG. 14, geometries of interest may be generated according to various embodiments. In FIG. 14, the geometries of the metal micro-structures 141 may be generated with CAD software, may be laser cut into metallic foils 142 of desired thickness (e.g., 0.001", or ~25 μm), and chemical etched and/or electropolished as shown for the microstructures 143 in order to refine the features of the micro-structures. For example, the metal microstructures may be fabricated by laser patterning a 2D design of interest in photoresist on both sides of a 0.001" (~25 μm) thick stainless steel or nitinol foil. The foil is then chemically etched and electropolished, leaving a thin extruded 2D structure. This design and fabrication process will allow production of any number of geometries for metal microstructures, as well as allow for design iterations to be turned around quickly. Metal microstructures fabricated may be extruded 2D structures with an internal bend radius greater than or equal to the 0.001" material thickness. The tip area of the features of the metal microstructures may be limited by the thickness of the foil (e.g., 0.001" or ~25 μm).

In another example, with respect to polymer microstructures, a method is provided for fabricating polymer microstructures. Polymer microstructures provide versatility during production. The minimum feature sizes of polymer microstructures may be smaller than metal microstructures, and the independent fabrication of molds and the molded microstructures may allow for the independent tailoring of geometry, molded polymer chemistry, and material properties to specific structural and mechanical requirements. Additionally, the number, density, and organization of the polymer microstructures may be controlled.

In particular, the combination of polymer material tunability and co-molding different polymers into 3D structures may provide an approach for transitioning from hard polymers in contact with the hard surface of a stent to more compliant polymers in contact with soft tissue as a risk mitigation in case mismatched mechanical properties limit the efficacy of a single material.

Figure 15:
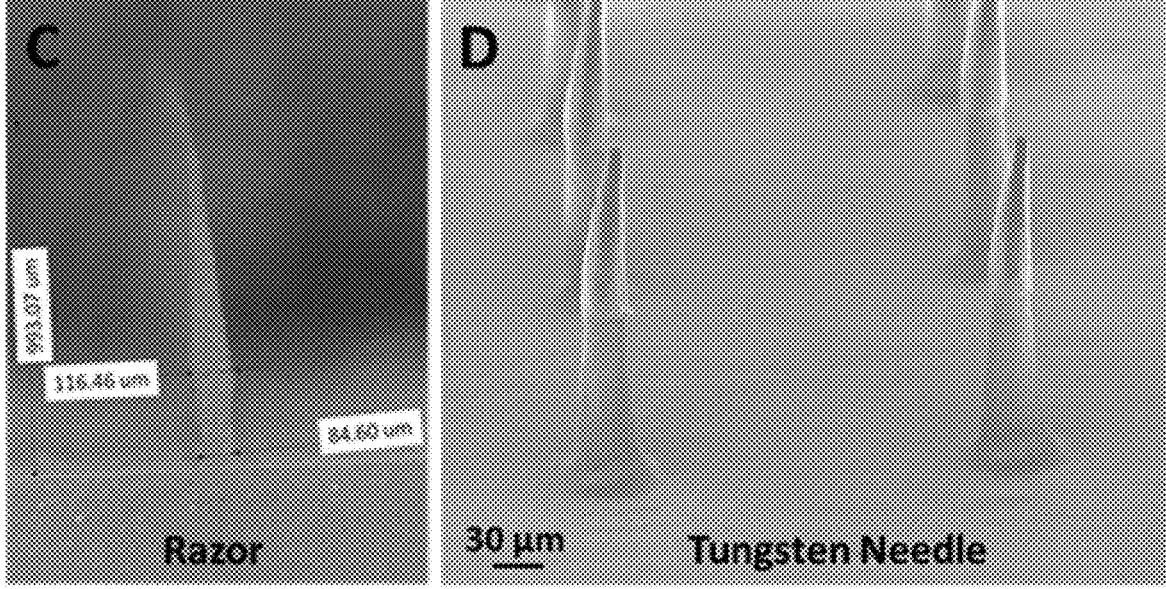
FIG. 15 is a magnified image of polymer microstructures.

In another example, a method is provided for fabricating polymer microstructures. As shown in FIG. 14, the method of fabricating polymer microstructures may comprise creating prototype molds using wax 144 and polymer sheets 145 (e.g., using low durometer machinist's wax and 0.004" polyethylene sheets); laminating the polymer sheets to the top of the wax using heat and pressure; and allowing the wax to flow and create a secure, flat surface. Additionally, a razor or tungsten needle 146 may be indented into the bilayer, creating a re-entrant mold microstructure profile 147. Biocompatible polymer materials, including but not limited to urethanes or silicones, may then be poured into the mold and cured. To remove the structures, the wax may be dissolved in acetone and the polyethylene may be peeled away. FIG. 15 illustrates example structures with re-entrant profiles created using such a bilayer molding technique. Specifically, FIG. 15(C) shows a ~1 mm tall linear structure 151 created with a razor blade indented into the bilayer to form the re-entrant mold. With reference to FIG. 15D, ~150 μm tall pillars with a re-entrant profile is created with a tungsten needle.

In further examples, the method for fabricating polymer microstructures may comprise molding structures into a bilayer wax/polymer mold is formed using a novel non-cleanroom-based indentation method adapted from microwedge machining. When the needle or razor is indented into a rigid plastic material, like the machinist's wax described above as an example for the bilayer mold, the wax plastically deforms and maintains the shape of the indenter needle/razor. When the needle/razor is indented into a plastic/elastic polymer material without usage of a rigid plastic material, the material may rebound some amount from the size of the needle/razor, creating a narrower indentation. However, if a bilayer approach is used (e.g., the machinist's wax and polyethylene, which may be provided as polyethylene sheets having a thickness of ~0.004"), the indentation in the bottom plastic/wax layer may be wider than the upper elastic polymer layer (e.g., polyethylene) due to the rebound, creating a mold with a re-entrant profile. As such, the indent may have a first profile in the plastic/elastic polymer and a second profile where the indent terminates in the rigid plastic (i.e., wax), with the first profile being narrower than the second profile due to the rebounding. Depending on the adhesion between the two mold materials of the bilayer mold, an abrupt or gradual transition can be created. The bilayer mold indentation enables rapid and low-cost fabrication of microstructures with a re-entrant profile that is accessible to researchers.

Figure 16:
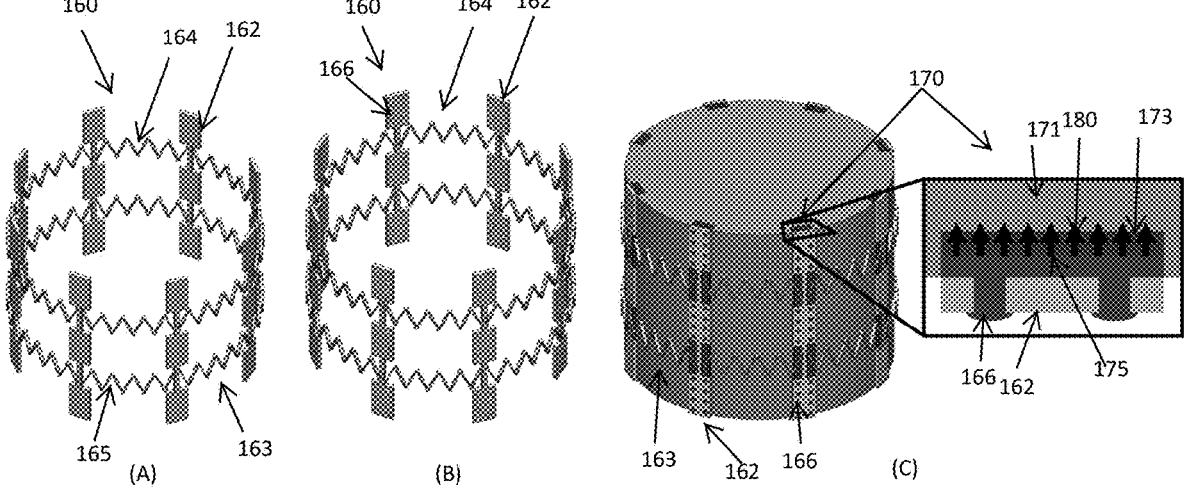
FIG. 16 is an image of polymer microstructures integrated into a stent.
Figure 17:
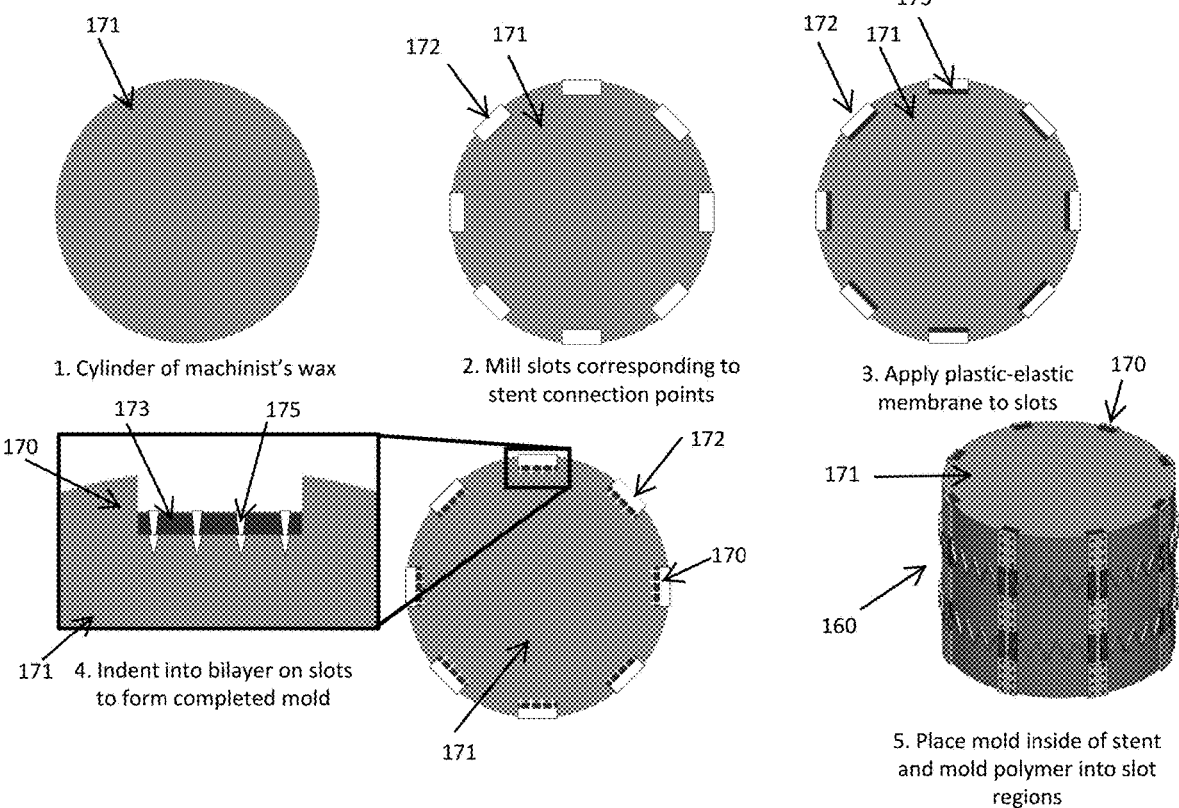
FIG. 17 is a schematic drawing of a method for integrating polymer microstructures into a stent.

Referring to FIGS. 16-17, polymer microstructures may also be integrated into a stent 160. With reference to FIG. 16(A), the stent 160 includes tabs 162 and a plurality of cylindrical rings 163 with interconnected struts 164. Adjacent struts 164 are connected at an apex 165 to allow the stent 160 to radially expand and contract as the struts 164 bend about the apex 165. In at least one embodiment, prefabricated strips of polymer microstructures described herein and fabricated by the methods described herein, are orientated parallel to the stent struts 164, and may be adhered directly to the tabs 162. As shown in FIG. 16(B), the stent 160 may include tabs 162 with mechanical interlocks 166 for overmolding. In at least a further embodiment, a partially cured polymer overmold is fused with a partially cured polymer microstructure strip. As shown in FIG. 16(C), overmolding and microstructure fabrication may be achieved in a single manufacturing step using the bilayer mold 170 described herein and with reference to FIG. 14 such that the bilayer mold 170 (i.e., the rigid plastic (e.g., wax) layer 171 and polyethylene sheet 173) can be removed after fabrication to form the polymer microstructure 180 via the needle/razor punched indents 175 in the bilayer mold 170.

With reference to FIG. 17, in at least another example, a cylinder 171 of a rigid plastic material, such as machinist's wax, is provided, and slots 172 may be milled into the wax cylinder 171 at locations corresponding to the stent connection points (e.g., corresponding to the tabs 162). A plastic-elastic membrane (e.g., polyethylene) 173 may then be applied to the milled slots 172 in the cylinder 171 to form the bilayer 174. As shown in FIG. 17, an indent 175 may then be made into the bilayer 174 on the slots 172 to form a completed mold 170. The mold 170 may then be placed inside of the stent 160, and the polymer microstructures may be molded into the slot regions 172 via the mold 170. The cylinder 171 and mold 170 can then be removed (e.g., via dissolving and/or peeling away) upon formation of the polymer microstructures.

As mentioned above, the microstructures may be able to penetrate into BHV tissue/material, provide adhesion strength that may withstand anticipated in vivo forces, and provide at least comparable performance to suturing and an advantage over controls such as non-re-entrant (e.g., straight) microneedles and bioglues. In addition, to further simulate conditions within the body, tests of the mechanical performance must be performed while wet or submerged, which requires customized testing systems for benchmarking and performance.

Prophetic Example: Method for Attaching a
Pediatric Heart Valve to a Polymer
Microstructure-Integrated Stent and for Measuring
Assembly Time The valve will be attached to the polymer microstructure-integrated stent by inflation with saline or a pediatric balloon catheter (e.g., NuMed for Children). Puncture force data for selected microstructures may be used to determine the target pressure for the balloon to engage tissue adhesion. The valve will be visually inspected for damage or anomalies prior to placement over the balloon. The stent will be secured in a fixture to facilitate stent alignment with the valve on the balloon. The balloon and valve may be placed within the stent and carefully expanded to the target pressure and external diameter of around 13.4+/−0.2 mm (equal to the internal diameter of the stent). The balloon will then be deflated and removed. Sutured control devices may be assembled with a minimum of 24 sutures (at least 3 sutures along each of the 8 longitudinal struts). Integration time for the microstructures and sutured devices will be recorded.

By simplifying the fabrication process, a time and cost savings over conventional methods is expected and will be quantified through this method. The data can be used as an approximate scaling factor to predict expected time and cost savings at scale. Valve competency may be checked via forward and back flow to ensure the leaflets open and close, respectively. Devices that pass this initial quality check will be subjected to hydrodynamic flow testing.

What is claimed is:

1. A bilayer mold for forming polymer microstructures, the bilayer mold comprising:
   a rigid plastic cylinder having slots defined along an outer periphery of the rigid plastic cylinder;
   a layer of plastic elastic polymer material disposed within the slots and having indents defined therethrough and in the rigid plastic cylinder,
   wherein the indents have a first profile which extends through the layer of plastic elastic polymer and terminates within the rigid plastic cylinder.

2. The bilayer mold of claim 1, wherein the indents have a second profile in the rigid plastic cylinder, different from the first profile.

3. The bilayer mold of claim 2, wherein the first profile is narrower than the second profile to form a re-entrant mold.

4. The bilayer mold for claim 1, wherein the rigid plastic cylinder is formed of wax.

5. The bilayer mold of claim 3, wherein the wax is machinist's wax.

6. The bilayer mold of claim 1, wherein the layer of plastic elastic polymer material is polyethylene.

\* \* \* \* \*